US012611469B2

(12) United States Patent
Mahajan et al.

(10) Patent No.: US 12,611,469 B2
(45) Date of Patent: Apr. 28, 2026

(54) PROMOTER SPECIFIC FOR NON-PIGMENTED CILIARY EPITHELIAL CELLS

(71) Applicants: The Board of Trustees of the Leland Stanford Junior University, Stanford, CA (US); The United States Government as represented by the Department of Veterans Affairs, Washington, DC (US)

(72) Inventors: Vinit Mahajan, Palo Alto, CA (US); Katherine J. Wert, Dallas, TX (US)

(73) Assignees: The Board of Trustees of the Leland Stanford Junior University, Stanford, CA (US); The United States Government as represented by the Department of Veterans Affairs, Washington, DC (US)

( * ) Notice: Subject to any disclaimer, the term of this patent is extended or adjusted under 35 U.S.C. 154(b) by 1073 days.

(21) Appl. No.: 17/762,591

(22) PCT Filed: Sep. 24, 2020

(86) PCT No.: PCT/US2020/052441
§ 371 (c)(1),
(2) Date: Mar. 22, 2022

(87) PCT Pub. No.: WO2021/061946
PCT Pub. Date: Apr. 1, 2021

(65) Prior Publication Data
US 2022/0362407 A1      Nov. 17, 2022

Related U.S. Application Data

(60) Provisional application No. 62/905,910, filed on Sep. 25, 2019.

(51) Int. Cl.
| | |
|---|---|
| *A61K 48/00* | (2006.01) |
| *A61K 31/7088* | (2006.01) |
| *A61K 38/46* | (2006.01) |
| *C12N 5/079* | (2010.01) |
| *C12N 9/22* | (2006.01) |
| *C12N 15/11* | (2006.01) |
| *C12N 15/86* | (2006.01) |

(52) U.S. Cl.
CPC ...... *A61K 48/0058* (2013.01); *A61K 31/7088* (2013.01); *A61K 38/465* (2013.01); *C12N 5/0621* (2013.01); *C12N 9/22* (2013.01); *C12N 15/11* (2013.01); *C12N 15/86* (2013.01); *C12N 2310/20* (2017.05); *C12N 2740/15043* (2013.01); *C12N 2740/15045* (2013.01); *C12N 2800/80* (2013.01)

(58) Field of Classification Search
None
See application file for complete search history.

(56) References Cited

U.S. PATENT DOCUMENTS

| | | | | |
|---|---|---|---|---|
| 2012/0129254 A1* | 5/2012 | Bisgrove | ............ | C12N 15/8217 |
| | | | | 435/351 |
| 2012/0258493 A1 | 10/2012 | Ernst et al. | | |
| 2014/0256802 A1 | 9/2014 | Boye et al. | | |
| 2018/0155789 A1* | 6/2018 | Maeder | ............... | C12N 15/102 |
| 2019/0216857 A1 | 7/2019 | Pena et al. | | |

FOREIGN PATENT DOCUMENTS

| | | |
|---|---|---|
| CN | 109790517 A | 5/2019 |
| CN | 109890964 A | 6/2019 |

OTHER PUBLICATIONS

Yu et al., Bestrophin-2 mediates bicarbonate transport by goblet cells in mouse colon. J Clin Invest. (2010), 120: 1722-1735 (Year: 2010).*
Cui et al., Forkhead transcription factor FoxA1 regulates sweat secretion through Bestrophin 2 anion channel and Na—K—Cl cotransporter 1. PNAS (2012), 109: 1199-1203 (Year: 2012).*
NC_000019.10, *Homo sapiens* chromosome 19, GRCh38.p12 Primary Assembly, position 12,751,000 through 12,758,458, https://www.ncbi.nlm.nih.gov/nuccore/NC_000019.10, [retrieved May 9, 2025]) (Year: 2018).*
Zhang et al., Bestrophin 2 is expressed in human non-pigmented ciliary epithelium but not retinal pigment epithelium. Molecular Vision (2010), 16: 200-206 (Year: 2010).*
Klinge, Estrogen receptor interaction with estrogen response elements. Nucleic Acids Research (2001), 29: 2905-2919 (Year: 2001).*
Lehmann et al., Spontaneous uptake of biologically active recombinant DNA by mammalian cells via a selected DNA segment. Gene Therapy (2005), 12: 446-51 (Year: 2005).*
Bakall et al., Bestrophin-2 is involved in the generation of intraocular pressure. Investigative Ophthalmology & Visual Science, (2008), 49: 1563-1570 (Year: 2008).*
Dryden et al., The transcription factor Erg controls endothelial cell quiescence by repressing activity of nuclear factor (NF)-$_K$B p. 65. Journal of Biological Chemistry (2012), 287: 12331-12342 (Year: 2012).*

(Continued)

*Primary Examiner* — Catherine Konopka
(74) *Attorney, Agent, or Firm* — Jenny L. Buchbinder; Bozicevic, Field & Francis LLP

(57) ABSTRACT

A construct comprising a promoter specific for non-pigmented ciliary epithelial cells (NPCECs) is provided. In particular, the construct comprises a BEST2 minimal promoter that confers NPCEC-specific expression. The BEST2 minimal promoter may be operably linked to an expressible sequence such as a gene encoding a polypeptide of interest, a regulatory RNA sequence, a reporter gene, and the like. Such constructs may be provided in an expression vector, for example, with the BEST2 minimal promoter operably linked to an expressible sequence or in a host cell genetically modified with such an expression vector.

25 Claims, 19 Drawing Sheets

Specification includes a Sequence Listing.

(56)          References Cited

OTHER PUBLICATIONS

Yoshioka et al., Development of a mono-promoter driven CRISPR/Cas9 system in mammalian cells. Scientific Reports (2015), 5: 18341, 1-8 (Year: 2015).*

Yu et al., Simultaneous Knockout of CXCR4 and CCR5 Genes in CD4+ T Cells via CRISPR/Cas9 Confers Resistance to Both X4- and R5-Tropic Human Immunodeficiency Virus Type 1 Infection. Human Gene Therapy (2018), 29: 51-67 (Year: 2018).*

Haberle and Stark, Eukaryotic core promoters and the functional basis of transcription initiation. Nature Reviews Molecular Cell Biology (2018), 19(10): 621-637 (Year: 2018).*

Genbank NC_000074.7, Mus Musculus strain C57BL/6J chromosome 8, GRCm39, region displayed position 85,733,831-85,742200, reverse complement shown, https://www.ncbi.nlm.nih.gov/nuccore/NC_000074.7, [retrieved May 9, 2025] (Year: 2024).*

Bakall, Bet al. Bestrophin-2 is Involved in the Generation of Intraocular Pressure. Investigative Ophthalmology and Visual Science. Apr. 2008, vol. 49, No. 4; pp. 1563-1570.

Doe Joint Genome Institute, et al. *Homo sapiens* chromosome 19 clone CTD-2659N19, complete sequence; GenBank: AC018761.6 (online). Sep. 28, 2001 Retrieved from the Internet: URL: https://www.ncbi.nlm.nih.gov/nucleotide/AC018761.6); pp. 1-6.

Fu, S et al. Eukaryotic synthetic construct chromosome 19; GenBank: CP034522.1 [online]. Dec. 11, 2018 [retrieved Jan. 26, 2021]. Retrieved from the Internet: URL: https://www.ncbi.nlm.nih.gov/nucleotide/CP034522.1; pp. 1-2.

Fu, S et al. Eukaryotic synthetic construct chromosome 19; GenBank: CP034497.1 [online]. Dec. 11, 2018 [retrieved Jan. 26, 2021]. Retrieved from the Internet: URL: https://www.ncbi.nlm.nih.gov/nucleotide/CP034497.1; pp. 1-2.

\* cited by examiner

PE

NPE

Chr19: 12,751,903

3'

BEST2: chr19: 12,751,702-12,758,458

Chr19: 12,749,703

| Name of Virus | Lot Number | Date | Purification Method | Production Sale (# of T75 flasks) | Final Volume (ml) | Infectious Titer (IU/ml) |
|---|---|---|---|---|---|---|
| LentiCRISPRv2-noU6 EF1a-GFP | 1027 | 09/10/2018 | Ultracentrifugation | 3 | 12X10ul | 4.04E+08 |
| LentiCRISPRv2-noU6-BEST2.13-GFP | 1028 | 09/10/2018 | Ultracentrifugation | 3 | 12X10ul | 1.20E+08 |

FIG. 7B

LentiCRISPRv2-noU6-EF1a-GFP (LV # 1027)
Transfection of 293T cells with pLentiCRISPRv2-noU6-EF1a-GFP Phase, 20x                          Fluorescence, 20x

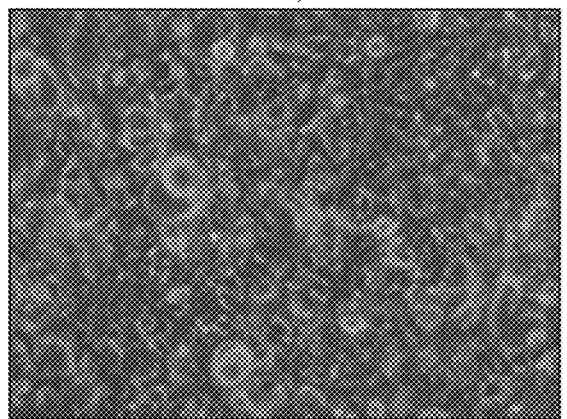 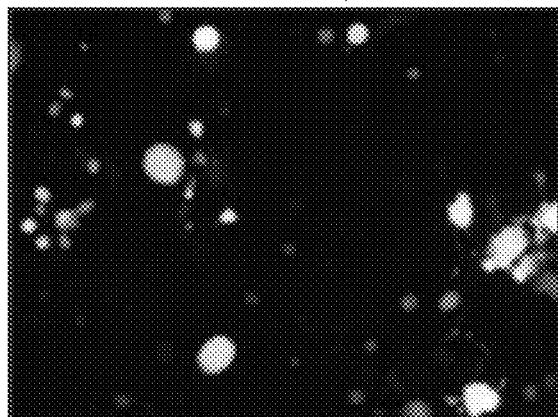

Infection of 293T with LentiCRISPRv2-noU6-EF1a-GFP

Phase, 20x                          Fluorescence, 20x

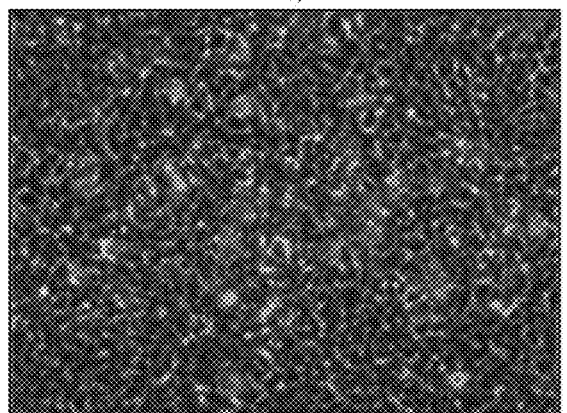 

*1 µl of the virus was used to infect 3e5 cells in 0.3 ml on a 24-well plate in the presence of 8 ug/ml polybrene. Results are shown 3 days post-infection.*

LentiCRISPRv2-noU6-BEST2.13-GFP (LV # 1028)
Transfection of 293T cells with pLentiCRISPRv2-noU6-BEST2.13-GFP Phase, 20x                                    Fluorescence, 20x Infection of 293T with LentiCRISPRv2-noU6-BEST2.13-GFP Phase, 20x                                    Fluorescence, 20x

*1 µl of the virus was used to infect 3e5 cells in 0.3 ml on a 24-well plate in the presence of 8 ug/ml polybrene. Results are shown 3 days post-infection.*

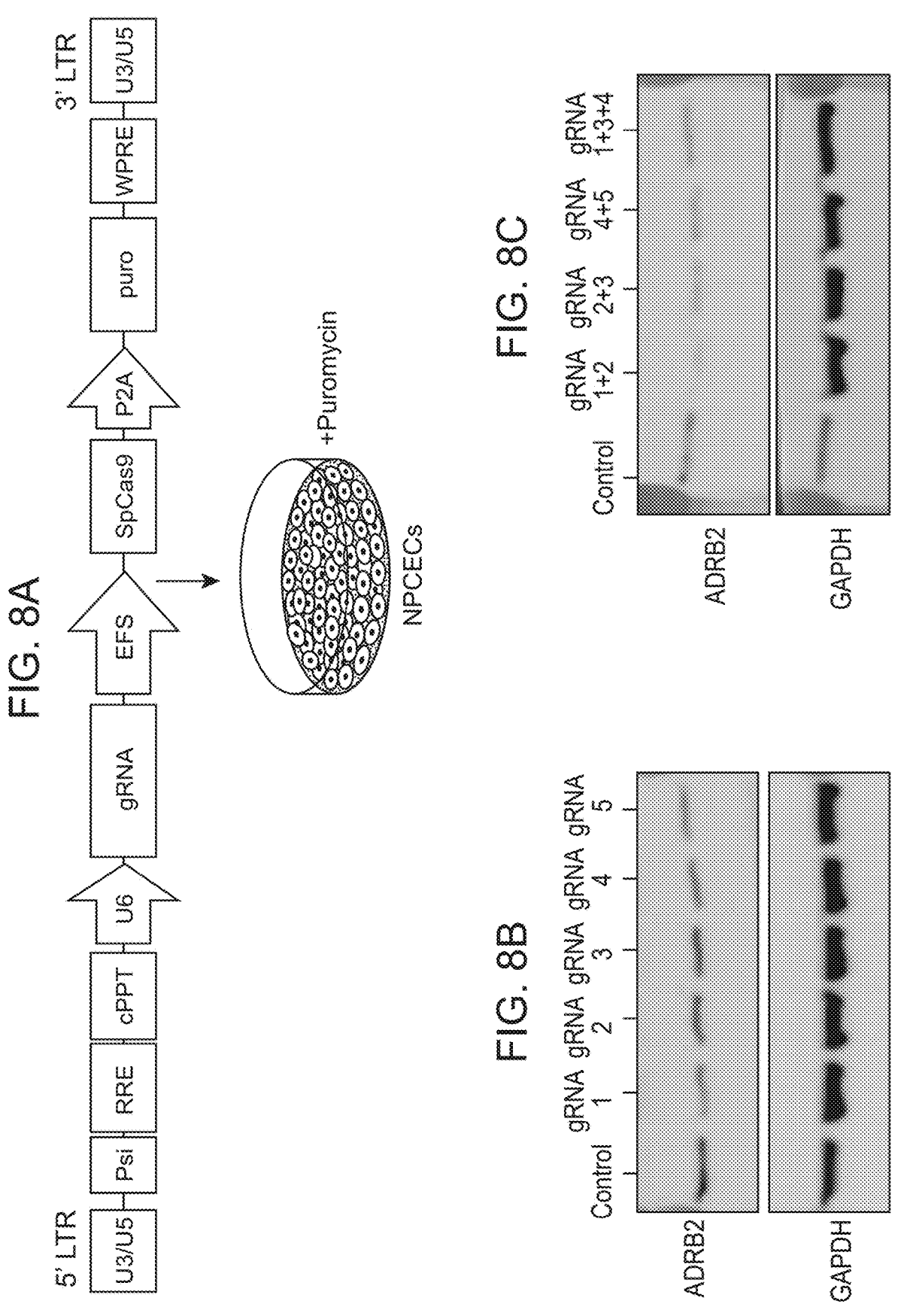

US 12,611,469 B2

1

PROMOTER SPECIFIC FOR NON-PIGMENTED CILIARY EPITHELIAL CELLS

INCORPORATION BY REFERENCE OF A SEQUENCE LISTING

A Sequence Listing is provided herewith as a Sequence Listing text file, "STAN-1602_S18-557WO_ST25" created on Aug. 11, 2021 and having a size of 769 bytes. The contents of the Sequence Listing text file are incorporated by reference herein in their entirety.

BACKGROUND

The ciliary body allows for the continual secretion of aqueous humor and the control of intraocular pressure (IOP). It is highly vascularized, and the non-pigmented ciliary epithelial cells (NPCECs) act as a barrier. The NPE has high metabolic activity (containing more mitochondria) and invaginations to provide a greater surface area for fluid secretion. The ciliary body not only plays a key role in eye diseases such as glaucoma but also contains many possible therapeutic targets, such as adrenergic alpha and beta receptors, dopamine receptors, prostaglandin receptors and peptide receptors. There remains a need for improved methods of gene therapy for treating eye diseases, in particular, for a cell-specific promoter for expressing genes selectively in the NPECECs of the ciliary body.

SUMMARY

A construct comprising a promoter specific for non-pigmented ciliary epithelial cells (NPCECs) is provided. In particular, the construct comprises a minimal BEST2 promoter that confers NPCEC-specific expression on genes operably linked thereto. The BEST2 minimal promoter may be operably linked to an expressible sequence such as a gene encoding a polypeptide of interest, a regulatory RNA sequence, a reporter gene, and the like. Such constructs may be provided in an expression vector, for example, with the BEST2 minimal promoter operably linked to an expressible sequence or in a host cell genetically modified with such an expression vector.

In one aspect, a recombinant NPCEC-specific promoter construct is provided comprising a DNA sequence comprising a BEST2 minimal promoter and a transcriptional start site (TSS).

In certain embodiments, the minimal BEST2 promoter comprises or consists of a nucleotide sequence corresponding to positions 12,751,703-12,751,803 of human chromosome 19. Although the foregoing numbering is relative to human chromosome 19, it is to be understood that the corresponding positions on chromosomes obtained from other mammalian species are also intended to be encompassed by the present invention.

In certain embodiments, the minimal BEST2 promoter comprises or consists of a nucleotide sequence selected from the group consisting of SEQ ID NO:1 and SEQ ID NO:2; or sequences displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto. The minimal promoter may be joined to non-native sequences providing additional functionality.

In certain embodiments, the construct further comprises one or more transcription factor binding sites, such as for transcription factors including, but not limited to, ZNF143, AP-2, KLF9, p63, KLF1, ER, EGR2, STAT5A, EGR3, Sp1, Sp4, MAZ, and ERG.

In certain embodiments, the construct further comprises one or more regulatory sequences operably linked to the minimal BEST2 promoter. For example, the construct may contain an enhancer and/or a regulatory sequence that makes the minimal BEST2 promoter inducible.

In some embodiments, the construct has a non-native configuration with a non-native spacing between the minimal BEST2 promoter and the TSS, a non-native spacing between the minimal BEST2 promoter and at least one regulatory sequence, or a non-native spacing between at least two regulatory sequences.

In some embodiments, the construct has a non-native TSS or a non-native regulatory sequence.

In certain embodiments, the construct further comprises an expressible sequence operably linked to the minimal BEST2 promoter. The expressible sequence may encode, for example, a polypeptide, a regulatory RNA, or a reporter.

In certain embodiments, the expressible sequence encodes a sequence-specific endonuclease. In some embodiments, the sequence specific endonuclease is a genome-editing enzyme. Exemplary genome-editing enzymes include, without limitation, Cas9 polypeptides, zinc finger nucleases, and transcription activator-like effector nucleases (TALENs). In one embodiment, the polypeptide-encoding sequence encodes an enzymatically inactive type II CRISPR/Cas polypeptide.

In certain embodiments, the construct further comprises a viral T2A peptide or IRES sequence operably linked to the minimal BEST2 promoter. In a nonlimiting example, the construct is multicistronic comprising a first expressible sequence encoding a Cas9 polypeptide and a second expressible sequence encoding a Cas9 guide RNA operably linked to the minimal BEST2 promoter.

In certain embodiments, the construct is double stranded. In some embodiments, the construct is a DNA or RNA construct.

In certain embodiments, the construct further comprises a nucleotide sequence encoding a reporter, wherein the nucleotide sequence encoding the reporter is operably linked to the minimal BEST2 promoter. In some embodiments, the reporter is a polypeptide that provides a detectable signal. For example, the reporter may be a fluorescent polypeptide including, without limitation, a red fluorescent protein, a green fluorescent protein, a blue fluorescent protein, or a yellow fluorescent protein. Alternatively, the reporter may be an enzyme that generates a detectable product upon acting on a substrate. For example, the reporter may include, without limitation, a luciferase such as a firefly, *Renilla*, or Metridia luciferase. In certain embodiments, the reporter is a mRNA.

In another aspect, an expression cassette comprising a construct described herein is provided, wherein the expression cassette is capable of providing gene expression specifically in NPCECs.

In another aspect, an expression vector comprising an expression cassette comprising any of the constructs described herein is provided.

In certain embodiments, the expression vector is a viral vector. In certain embodiments, the viral vector is a lentiviral vector. In some embodiments, the lentiviral vector comprises a long-terminal repeat (LTR), a 4 packaging signal, a rev response element (RRE), and a central polypurine tract (cPPT).

In certain embodiments, the expression vector further comprises a selection marker. For example, the selection marker may be an antibiotic resistance gene including, without limitation, a puromycin resistance gene, neomycin resistance gene, and an ampicillin resistance gene.

In certain embodiments, the expression vector further comprises a Woodchuck hepatitis virus post-transcriptional regulatory element (WPRE).

In certain embodiments, the expression vector further comprises a mammalian origin of replication, for example, including, without limitation, a simian virus 40 (SV40) origin of replication.

In certain embodiments, the expression vector further comprises a multiple cloning site.

In certain embodiments, the expression vector further comprises a polyadenylation site.

In certain embodiments, the expression vector further comprises an SV40 early promoter.

In certain embodiments, the expression vector is double stranded.

In certain embodiments, the expression vector is a DNA or RNA expression vector.

In another aspect, a NPCEC genetically modified with a construct, an expression cassette, or an expression vector described herein is provided. In some embodiments, the NPCEC is a transformed cell line or a primary cell. In some embodiments, the construct is integrated into the cell's genome.

In another aspect, a method of localizing expression of a gene product of interest to NPCECs in a mammalian subject is provided, the method comprising introducing an expression vector, described herein, comprising an expressible sequence encoding the gene product of interest operably linked to the minimal BEST2 promoter into an eye of the subject, wherein the gene product of interest is selectively expressed in the NPCECs.

In another aspect, a method of expressing a gene product of interest specifically in NPCECs is provided, the method comprising: a) transfecting an isolated cell, a cell line, or a population of cells with a construct described herein, wherein the minimal BEST2 promoter is operably linked to an expressible sequence encoding the gene product of interest; and b) culturing the isolated cell, the cell line, or the population of cells under conditions wherein the gene product of interest is expressed by the cell or cells if the cell or cells are NPCECs.

In another aspect, a kit is provided for expressing a gene in NPCECs, the kit comprising a construct, expression cassette, or expression vector described herein. The kit may further comprise instructions for expressing the gene in MPCECs. In certain embodiments, the kit comprises a construct, expression cassette, or expression vector comprising a minimal BEST2 promoter comprising or consisting of a nucleotide sequence selected from the group consisting of SEQ ID NO:1 and SEQ ID NO:2; or sequences displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIGS. 2A-2C show in vitro targeting of non-pigmented ciliary epithelial cells. FIG. 2A. A human retinal pigment epithelial cell line (ARPE19) and human non-pigmented ciliary epithelial cells (NPCECs) were transfected with a lentiviral construct containing green fluorescent protein (GFP) driven by the constitutively active EF1a (elongation factor 1 alpha) promoter. LTR, long-terminal repeat; U3/U5, Unique 3' or 5' region; Psi, RNA target site for packaging by nucleocapsid; RRE, Rev Response Element; cPPT, Central polypurine tract; PGK, phosphoglycerate kinase promoter; Puro, puromycin resistance gene; WPRE, Woodchuck hepatitis virus post-transcriptional regulatory element. FIG. 2B. GFP was detectable via fluorescence microscopy 24 hours post-transfection in both ARPE19 and NPCE cells. 5× magnification. FIG. 2C. FACs sorting showed an approximate 35% transfection efficiency of the lentiviral construct in both ARPE19 and NPCE cells.

FIGS. 4A-4C show size reduction of the VMD2L1 promoter driving preferential targeting of non-pigmented ciliary epithelial cells. FIG. 4A. The plasmid construct described in FIG. 3 was created containing green fluorescent protein (GFP) driven by the constitutively active EF1a (elongation factor 1 alpha) promoter, the sequence (promoter 1; chr19: 12,750,691-12,751,903) approximately 1.1 kb upstream of the BEST2 gene (chr19:12,751,702-12,758,458), and shortened versions down to 100 bp of this upstream region (promoters 2-14). FIG. 4B. A human retinal pigment epithelial cell line (ARPE19) and human non-pigmented ciliary epithelial cells (NPCECs) were transfected with a plasmid construct containing green fluorescent protein (GFP) driven by each of the promoters shown in the top panel (EF1a and promoters 1-14). Representative images of GFP positive cells are shown for the EF1a promoter (control) and promoters 1, 3, 4, 6, and 13 approximately 24 hours after transfection. 5× magnification. FIG. 4C. FACs sorting for the percent of GFP positive ARPE19 (black) or NPCE (gray) cells after transfection with promoters 1-14, normalized to the EF1a controls for each cell line. Promoter 13 (red box; 100 bp) showed a specificity for NPCE cells over ARPE19 cells.

FIG. 5A. Three additional promoter sequences (promoters 15-17; chr19:12,749,703-12,750,691) were designed upstream of promoter 1, in a second region suggested to contain a potential promoter for the BEST2 gene. FIG. 5B. A human retinal pigment epithelial cell line (ARPE19) and human non-pigmented ciliary epithelial cells (NPCECs) were transfected with a plasmid construct containing green fluorescent protein (GFP) driven by promoters 15-17 shown in the FIG. 5A (EF1a controls from FIG. 4 also shown). Representative images of GFP positive cells are shown for the EF1a promoter (control) and promoters 15-17 at approximately 24 hours after transfection. 5× magnification. No GFP was detectable for plasmids containing promoter 15-17.

FIG. 6A. The sequence regions for each of the tested 14 promoters approximately 1.1 kb upstream of the BEST2 gene, with some overlap into the BEST2 gene. FIGS. 6B-6C. The locations of transcription factors known to bind within the 1.2 kb region tested to drive GFP expression specifically in the non-pigmented ciliary epithelial cells (NPCECs). BEST2 gene is shown on the left-hand side. Dashed lines highlight the region overlapping with promoter 13 that showed specificity toward NPCECs.

FIGS. 7A-7E show in vivo preferential targeting of the non-pigmented ciliary epithelial cells using intravitreal injections of a VMD2L1-drived green fluorescent protein. FIG. 7A. Lentivirus was created containing green fluorescent protein (GFP) driven by either the constitutively active EF1a (elongation factor 1 alpha) promoter or promoter 13 for the BEST2 gene. FIGS. 7B-7C. Lentiviruses effectively transduced HEK293T cells and had a titer of $4 \times 10^8$ for EF1a and $1.2 \times 10^8$ for promoter 13 viral vectors. FIG. 7D. The promoter 13 region shares high homology between human (1, top sequence, SEQ ID NO:1) and mouse (2, bottom sequence, SEQ ID NO:2). FIG. 7E. Lentiviruses created in HEK293T cells will undergo intravitreal injection (arrows show injection sites in right diagram) into the mouse eye, to show specificity to the non-pigmented ciliary epithelial cells by GFP expression.

FIGS. 8A-8E show CRISPR/Cas9-mediated knockdown of beta-adrenergic receptor 2 in the non-pigmented ciliary epithelial cells. FIG. 8A. Human non-pigmented ciliary epithelial cells (NPCECs) were transfected with a lentiviral construct containing guide RNA (gRNA) against the beta-adrenergic receptor 2 (ADRB2) and SpCas9 driven by the constitutively active EFS (elongation factor 1 alpha short) promoter. LTR, long-terminal repeat; U3/U5, Unique 3' or 5' region; Psi, RNA target site for packaging by nucleocapsid; RRE, Rev Response Element; cPPT, Central polypurine tract; U6, type III RNA polymerase III promoter; P2A, porcine teschovirus-1 2A; Puro, puromycin resistance gene; WPRE, Woodchuck hepatitis virus post-transcriptional regulatory element. FIG. 8B. NPCECs transfected with control (no gRNA) or gRNAs 1-5 for ADRB2 were treated for at least 3 days with puromycin and then collected for western blot analysis. ADRB2 protein bands were normalized to GAPDH and each gRNA knocked down ADRB2 protein by approximately 50%. FIG. 8C. NPCECs transfected with control (no gRNA) or double and triple combinations of gRNAs 1-5 for ADRB2 were treated for at least 3 days with puromycin and then collected for western blot analysis. FIG. 8D shows ADRB2 knock-down in NPCECs transfected with gRNAs 1-5. FIG. 8E shows ADRB2 knock-down in NPCECs transfected with double and triple combinations of gRNAs 1-5. ADRB2 protein bands were normalized to GAPDH. Using two gRNAs knocked down ADRB2 protein by approximately 80-90%, with gRNA 1 and gRNA 2 showing the strongest knockdown of ADRB2 protein.

DETAILED DESCRIPTION

Figure 1:
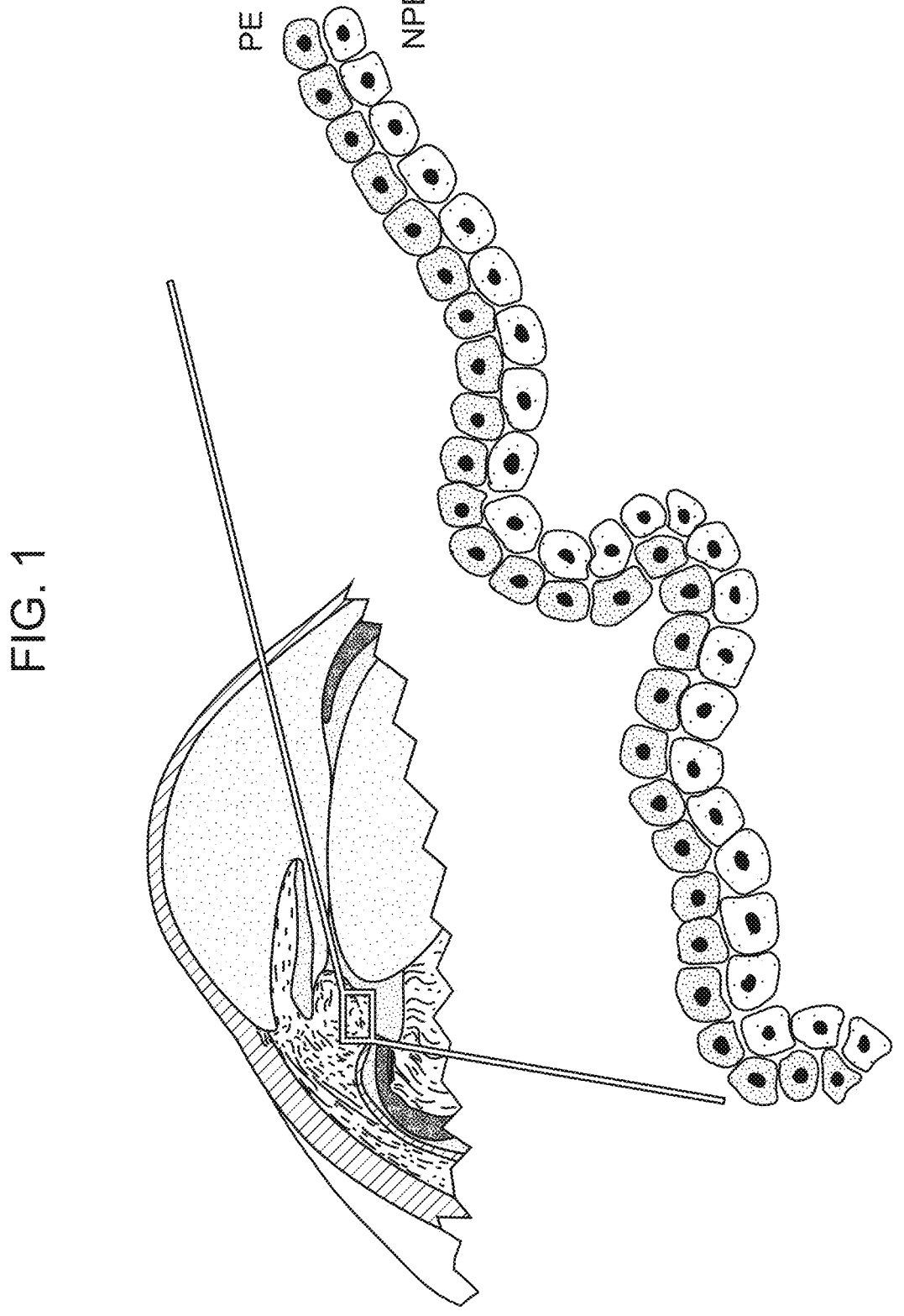
FIG. 1 shows a schematic of the location of the ciliary body within the human eye, which contains pigmented epithelium (PE) and non-pigmented epithelium (NPE).

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the vector" includes reference to one or more vectors and equivalents thereof, e.g. plasmids, constructs, and the like, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

In the description that follows, a number of terms conventionally used in the field are utilized. In order to provide a clear and consistent understanding of the specification and claims, and the scope to be given to such terms, the following definitions are provided.

The term "promoter" refers to the regulatory DNA region which controls transcription or expression of a gene and which can be located adjacent to or overlapping a nucleotide or region of nucleotides at which RNA transcription is initiated. A promoter contains specific DNA sequences which bind protein factors, often referred to as transcription factors, which facilitate binding of RNA polymerase to the DNA leading to gene transcription.

A "minimal promoter" or "core promoter" refers to a promoter which contains all the basic necessary elements to promote transcriptional expression of an operably linked polynucleotide.

A promoter may also include one or more "regulatory elements" which may also influence the expression or transcription by the promoter. Such regulatory elements encode specific DNA sequences which bind other factors, which may include but are not limited to enhancers, silencers, insulators, and/or boundary elements.

The term "operably linked", in the context of the present disclosure, means joined in such a fashion as to work together to allow transcription. In some embodiments, two polynucleotide sequences may be operably linked by being directly linked via a nucleotide bond. In this fashion, the two operably linked elements contain no intervening sequences and in being joined are able to direct transcription of an expression sequence. In other embodiments, two elements may be operably linked by an intervening compound, for instance a polynucleotide sequence of variable length. In such a fashion, the operably linked elements, although not directly juxtaposed, are still able to direct transcription of an expression sequence.

Thus, according to some embodiments, one or more promoter elements may be operably linked to each other, and additionally be operably linked to a downstream expression sequence, such that the linked promoter elements are able to direct expression of the downstream expression sequence.

The term "expressible sequence" refers to a polynucleotide which is operably linked to a promoter element such that the promoter element is able to cause transcriptional expression of the expression sequence. An expressible sequence is typically linked downstream, on the 3'-end of the promoter element(s) in order to achieve transcriptional expression. The result of this transcriptional expression is the production of an RNA macromolecule. The expressed RNA molecule may encode a protein and may thus be subsequently translated by the appropriate cellular machinery to produce a polypeptide/protein molecule. In some embodiments, the expression sequence may encode a reporter protein. Alternately, the RNA molecule may be an antisense, RNAi or other non-coding RNA molecule, which may be capable of modulating the expression of specific genes in a cell, as is known in the art.

The term "nucleic acid" as used herein includes any nucleic acid, and may be a deoxyribonucleotide or ribonucleotide polymer in either single or double-stranded form. A "polynucleotide" or "nucleotide polymer" as used herein may include synthetic or mixed polymers of nucleic acids, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), and modified linkages (e.g., alpha anomeric polynucleotides, etc.). Also included are synthetic molecules that mimic polynucleotides in their ability to bind to a designated sequence via hydrogen bonding and other chemical interactions.

A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a nucleic acid of interest and which can transfer nucleic acid sequences to target cells. Thus, the term includes cloning and expression vehicles, as well as viral vectors.

An "expression vector" is typically a nucleic acid molecule which is integrating or autonomous, (i.e. self-replicating), and which contains the necessary components to achieve transcription of an expressible sequence in a target cell, when introduced into the target cell. Expression vectors may include plasmids, cosmids, phage, YAC, BAC, minichromosomes, viruses, e.g. retroviruses, adenovirus, lentivirus, SV-40, and the like; etc. Many such vectors have been described in the art and are suitable for use with the NPCEC-specific promoters of the present invention. Expression vectors of the present invention include an NPCEC-specific promoter as described herein, operably linked to an expressible sequence, which may also be optionally operably linked to a transcription termination sequence, such as a polyadenylation sequence. The expression vector optionally contains nucleic acid elements which confer host selectivity, elements that facilitate replication of the vector, elements that facilitate integration of the vector into the genome of the target cell, elements which confer properties, for example antibiotic resistance, to the target cell which allow selection or screening of transformed cells and the like. Techniques and methods for design and construction of expression vectors are well known in the art.

"Substantially purified" generally refers to isolation of a substance (compound, polynucleotide, protein, polypeptide, peptide composition) such that the substance comprises the majority percent of the sample in which it resides. Typically in a sample, a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a protein, polypeptide, or peptide, that the indicated molecule is separate and discrete from the whole organism with which the molecule is found in nature or is present in the substantial absence of other biological macro molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome. "Recombinant" as used herein to describe a nucleic acid molecule means a polynucleotide of genomic, cDNA, viral, semisynthetic, or synthetic origin which, by virtue of its origin or manipulation, is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

The term "transformation" refers to the insertion of an exogenous polynucleotide into a host cell, irrespective of the method used for the insertion. For example, direct uptake or transduction are included. The exogenous polynucleotide may be maintained as a non-integrated vector, for example, a plasmid, or alternatively, may be integrated into the host genome.

"Recombinant host cells," "host cells," "cells", "cell lines," "cell cultures," and other such terms denoting micro-organisms or higher eukaryotic cell lines cultured as uni-cellular entities refer to cells which can be, or have been, used as recipients for recombinant vector or other trans-ferred DNA, and include the original progeny of the original cell which has been transfected.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence can be determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA, and even syn-thetic DNA sequences. A transcription termination sequence may be located 3' to the coding sequence.

Typical "control elements," include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence.

"Expression cassette" or "expression construct" refers to an assembly which is capable of directing the expression of the sequence(s) or gene(s) of interest. An expression cassette generally includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid or viral vector. In addition to the components of the expres-sion cassette, the plasmid or viral vector may also include, one or more selectable markers, a signal which allows the plasmid or viral vector to exist as single stranded DNA (e.g., a M13 origin of replication), at least one multiple cloning site, and a "mammalian" origin of replication (e.g., a SV40 or adenovirus origin of replication).

"Purified polynucleotide" refers to a polynucleotide of interest or fragment thereof which is essentially free, e.g., contains less than about 50%, preferably less than about 70%, and more preferably less than about at least 90%, of the protein with which the polynucleotide is naturally asso-ciated. Techniques for purifying polynucleotides of interest are well-known in the art and include, for example, disrup-tion of the cell containing the polynucleotide with a chao-tropic agent and separation of the polynucleotide(s) and proteins by ion-exchange chromatography, affinity chroma-tography and sedimentation according to density.

The term "transfection" is used to refer to the uptake of foreign DNA by a cell. A cell has been "transfected" when exogenous DNA has been introduced inside the cell mem-brane. A number of transfection techniques are generally known in the art. See, e.g., Graham et al. (1973) Virology, 52:456, Sambrook et al. (2001) Molecular Cloning, a labo-ratory manual, 3rd edition, Cold Spring Harbor Laborato-ries, New York, Davis et al. (1995) Basic Methods in Molecular Biology, 2nd edition, McGraw-Hill, and Chu et al. (1981) Gene 13:197. Such techniques can be used to introduce one or more exogenous DNA moieties into suit-able host cells. The term refers to both stable and transient uptake of the genetic material.

"Gene transfer" or "gene delivery" refers to methods or systems for reliably inserting DNA or RNA of interest into a host cell. Such methods can result in transient expression of non-integrated transferred DNA, extrachromosomal rep-lication and expression of transferred replicons (e.g., epi-somes), or integration of transferred genetic material into the genomic DNA of host cells. Gene delivery expression vec-tors include, but are not limited to, vectors derived from plasmid vectors, viral vectors, and non-viral vectors.

"Mammalian cell" refers to any cell derived from a mammalian subject suitable for transfection with a construct or vector comprising an NPCEC-specific promoter, as described herein. The cell may be xenogeneic, autologous, or allogeneic. The cell can be a primary cell obtained directly from a mammalian subject. The cell may also be a cell derived from the culture and expansion of a cell obtained from a mammalian subject. Immortalized cells are also included within this definition. In some embodiments, the cell has been genetically engineered to express a recom-binant protein and/or nucleic acid.

The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, i.e., an .alpha. carbon that is bound to a hydrogen, a carboxyl group, an amino group, and an R group, e.g., homoserine, norleucine, methionine sulfoxide, methionine methyl sulfo-nium. Such analogs have modified R groups (e.g., norleu-cine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. In some embodiments, the mammal is human.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

NPCEC-Specific Promoter Constructs

The present disclosure provides a NPCEC-specific promoter construct comprising a minimal BEST2 promoter and a transcription start site. The NPCEC-specific promoter may be operably linked to an expressible sequence such as a gene encoding a polypeptide of interest, a regulatory RNA sequence, a reporter gene, and the like. Such constructs may be provided in an expression vector, for example, with the minimal BEST2 promoter operably linked to an expressible sequence. Also provided are host cells genetically modified with the construct comprising the NPCEC-specific promoter, which may be integrated into a host cell chromosome or an expression vector to control production of an expressible sequence.

In certain embodiments, the minimal BEST2 promoter comprises or consists of a nucleotide sequence corresponding to positions 12,751,703-12,751,803 of human chromosome 19. Although the foregoing numbering is relative to human chromosome 19, it is to be understood that the corresponding positions on chromosomes obtained from other mammalian species are also intended to be encompassed by the present invention. In certain embodiments, the minimal BEST2 promoter comprises or consists of a nucleotide sequence selected from the group consisting of SEQ ID NO:1 and SEQ ID NO:2; or sequences displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto.

The "promoter" comprises a regulatory DNA region which controls transcription or expression of a gene that is located adjacent to or overlapping a site at which RNA transcription is initiated (i.e., the transcriptional start site (TSS)). The promoter may also contain one or more specific DNA sequences which bind transcription factors, which facilitate binding of RNA polymerase to the DNA to initiate gene transcription. A "minimal promoter" or "core promoter" contains all the basic necessary elements to promote transcriptional expression of an operably linked expressible sequence. A promoter may also include one or more "regulatory elements" which influence the expression or transcription by the promoter. Such regulatory elements comprise specific DNA sequences which bind other factors, which may include, but are not limited to, enhancers, silencers, insulators, and boundary elements. In certain embodiments, the NPCEC-specific promoter construct further comprises one or more transcription factor binding sites, such as for transcription factors including, but not limited to, ZNF143, AP-2, KLF9, p63, KLF1, ER, EGR2, STAT5A, EGR3, Sp1, Sp4, MAZ, and ERG.).

In some embodiments, the construct has a non-native configuration with a non-native spacing between the BEST2 minimal promoter and the TSS, and/or a non-native spacing between the BEST2 minimal promoter and at least one regulatory element, and/or a non-native spacing between regulatory elements. In certain embodiments, the regulatory elements are directly joined with no intervening sequences in the construct. In other embodiments, the regulatory elements are operably linked with intervening sequences. In general the spacing between the regulatory elements is not more than about 15 KB, generally not more than about 10 KB, usually not more than about 1 KB, more often not more than about 500 nt, and may be not more than about 100 nt, down to a direct joining of the two sequences.

In some embodiments, the promoter or TSS is modified with respect to the native regulatory and/or native core promoter sequence or TSS. In general, such modifications will not change the functional activity of the promoter with respect to cell-type selectivity; and the rate of transcription in cells where the promoter is active. A modified BEST2 promoter provides for a transcription rate of an expressible sequence operably linked to the modified BEST2 promoter sequence that is at least about 75% of the transcription rate of the promoter sequence of SEQ ID NO: 1 or 2, at least about 80%, at least about 90%, at least about 95%, at least about 99%, or more. Methods of assessing promoter strength and selectivity are known in the art, including, for example, expression of a reporter sequence in a cell in vivo or in vitro, and quantitating the reporter activity.

In some embodiments, the promoter is inducible and contains a regulatory sequence that allows for control of expression of an expressible sequence in a host cell. The regulatory sequence that controls expression can be operably linked to the minimal BEST2 promoter and positioned upstream of the minimal BEST2 promoter. Such regulatory sequences are known to those of skill in the art, and examples include those which cause the expression of a gene to be turned on or off in response to a chemical or physical stimulus, including the presence of a regulatory compound. The regulatory sequence used to control expression may be endogenous or exogenous to the mammalian host. In some embodiments, bacterial gene control elements in combination with viral transactivator proteins are used to provide mammalian inducible expression. Examples of mammalian-compatible regulatory sequences include those capable of controlling an engineered promoter to adjust transcription in response to antibiotics including, without limitation, tetracyclines, streptogramins, and macrolides. For example, inclusion of a bacterial tetracycline response element (TRE) in a construct allows mammalian expression to be induced by tetracycline or a derivative thereof (e.g., doxycycline). See, e.g., Weber et al. (2004) *Methods Mol. Biol.* 267:451-66, Das et al. (2016) *Curr. Gene Ther.* 16 (3): 156-67, Chruscicka et al. (2015) *J. Biomol. Screen.* 20 (3): 350-8, Yarranton (1992) *Curr. Opin. Biotechnol.* 3 (5): 506-11, Gossen & Bujard (1992) *Proc. Natl. Acad. Sci. U.S.A.* 89 (12): 5547-51, Gossen et al. (1995) *Science* 268 (5218): 1766-9; herein incorporated by reference.

An expressible sequence of interest can be placed under the control of the minimal BEST2 promoter so that the sequence of interest is transcribed into RNA in a host NPCEC. Expressible sequences of interest may include without limitation, genes encoding polypeptides of interest, RNAi or regulatory RNA sequences, or reporter genes. In some embodiments, the expressible sequence is operably linked to the minimal promoter in the construct.

In some embodiments, the expressible sequence is a polynucleotide encoding a RNA interference (RNAi) nucleic acid or regulatory RNA of interest such as, but not limited to, a microRNA (miRNA), a small interfering RNA (siRNA), a short hairpin RNA (shRNA), a small nuclear RNA (snRNA), a long non-coding RNA (lncRNA), an antisense nucleic acid, and the like. The nucleotide sequence encoding the RNAi nucleic acid or regulatory RNA may be operably linked to the minimal promoter to allow production of the RNAi nucleic acid or regulatory RNA by transcription in a suitable host cell.

In some embodiments, the expressible sequence is a polynucleotide encoding a polypeptide of interest. The polypeptide of interest may be any type of protein/peptide including, without limitation, an enzyme, an extracellular matrix protein, a receptor, transporter, ion channel, or other membrane protein, a hormone, a neuropeptide, an antibody, or a cytoskeletal protein; or a fragment thereof, or a biologically active domain of interest.

In some embodiments, the polypeptide of interest is a sequence specific endonuclease for use in genome editing. The sequence specific endonuclease is used to create a double-stranded break at a specific site in the genome, wherein the NPCEC-specific promoter construct is used to localize production of the sequence-specific endonuclease to NPCECs. The double stranded breaks can then be repaired by non-homologous end joining (NHEJ), microhomology-mediated end joining (MMEJ), or homology-directed repair (HDR) pathways. Desired genome edits can be introduced into the genome using donor DNA to repair double-strand breaks by homologous recombination. Various sequence-specific endonucleases can be used in genome editing for creation of double-strand breaks in DNA, including, without limitation, engineered zinc-finger nucleases (ZFNs), transcription activator-like effector nucleases (TALENs), and clustered regularly interspaced short palindromic repeats (CRISPR) Cas9. See, e.g., *Targeted Genome Editing Using Site-Specific Nucleases: ZFNs, TALENs, and the CRISPR/Cas9 System* (T. Yamamoto ed., Springer, 2015); *Genome Editing: The Next Step in Gene Therapy* (Advances in Experimental Medicine and Biology, T. Cathomen, M. Hirsch, and M. Porteus eds., Springer, 2016); Aachen Press *Genome Editing* (CreateSpace Independent Publishing Platform, 2015); herein incorporated by reference. Precise control over the timing of production of the genome editing enzyme can be achieved by including a regulatory sequence in the promoter construct that makes the minimal BEST2 promoter inducible and operably linking a recombinant polynucleotide encoding the genome editing enzyme to the inducible promoter to allow turning on and off of expression as desired.

Exemplary reporter genes that may be included in constructs include, without limitation, those that encode fluorescent or luminescent proteins, such as red fluorescent protein, green fluorescent protein, blue fluorescent protein, yellow fluorescent protein, and the like. Alternatively, the reporter may be an enzyme that generates a detectable product upon acting on a substrate, such as a luciferase (e.g., a firefly, *Renilla*, or Metridia luciferase), which catalyzes a reaction with luciferin to produce light. In certain embodiments, the reporter gene is linked to a gene of interest to monitor expression of the gene of interest. In certain embodiments, the reporter is a mRNA.

A coding sequence may or may not contain a signal peptide or leader sequence. Either naturally occurring signal peptides or heterologous sequences can be used. Leader sequences can be removed by the host in post-translational processing. Control sequences and other regulatory sequences may be ligated to the coding sequence prior to insertion into a vector comprising the inducible promoter construct. Alternatively, the coding sequence can be cloned directly into an expression vector that already contains the control sequences and an appropriate restriction site.

In some cases, it may be necessary to modify the coding sequence so that it may be attached to the control sequences with the appropriate orientation; i.e., to maintain the proper reading frame. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; *DNA Cloning*, Vols. I and II, supra; *Nucleic Acid Hybridization* (S. Lukyanov ed., Springer, 2007).

An expression vector comprising the minimal BEST2 promoter construct operably linked to an expressible sequence encoding a gene product of interest can be used to transform an isolated cell, a cell line, or a population of cells, wherein the gene product of interest is selectively expressed by the cell or cells if the cell or cells are NPCECs. In some embodiments, the gene product is a protein that is secreted. The transformed cells secrete the protein product into the surrounding media. Certain regulatory sequences can be included in the vector to enhance secretion of the protein product, for example using a tissue plasminogen activator (TPA) leader sequence, an interferon (γ or α) signal sequence or other signal peptide sequences from known secretory proteins. The secreted protein product can then be isolated by various techniques described herein, for example, using standard purification techniques such as but not limited to, hydroxyapatite resins, column chromatography, ion-exchange chromatography, size-exclusion chromatography, electrophoresis, HPLC, immunoadsorbent techniques, affinity chromatography, immunoprecipitation, and the like.

Alternatively, the protein is not secreted, and transformed cells are disrupted, using chemical, physical or mechanical means, which lyse the cells yet keep the recombinant protein substantially intact. Intracellular proteins can also be obtained by removing components from the cell membrane, e.g., by the use of detergents or organic solvents, such that leakage of the polypeptides occurs. Such methods are known to those of skill in the art and are described in, e.g., *Protein Purification Applications: A Practical Approach*, (Simon Roe, Ed., 2001).

For example, methods of disrupting cells include but are not limited to: sonication or ultrasonication; agitation; liquid or solid extrusion; heat treatment; freeze-thaw; desiccation; explosive decompression; osmotic shock; treatment with lytic enzymes including proteases such as trypsin, neuraminidase and lysozyme; alkali treatment; and the use of detergents and solvents such as bile salts, sodium dodecylsulfate, Triton, NP40 and CHAPS. The particular technique used to disrupt the cells is largely a matter of choice and will depend on the cell type in which the polypeptide is expressed, culture conditions and any pretreatment used.

Following disruption of the cells, cellular debris is removed, generally by centrifugation, and the intracellularly produced peptides or polypeptides are further purified, using standard purification techniques such as but not limited to, column chromatography, ion-exchange chromatography, size-exclusion chromatography, electrophoresis, HPLC, immunoadsorbent techniques, affinity chromatography, immunoprecipitation, and the like.

For example, one method for obtaining the intracellular proteins involves affinity purification, such as by immuno-affinity chromatography using antibodies (e.g., previously generated antibodies), or by lectin affinity chromatography. Particularly preferred lectin resins are those that recognize mannose moieties such as but not limited to resins derived from *Galanthus nivalis* agglutinin (GNA), *Lens culinaris* agglutinin (LCA or lentil lectin), *Pisum sativum* agglutinin (PSA or pea lectin), *Narcissus pseudonarcissus* agglutinin (NPA) and *Allium ursinum* agglutinin (AUA). The choice of a suitable affinity resin is within the skill in the art. After affinity purification, expressed proteins can be further purified using conventional techniques well known in the art, such as by any of the techniques described above.

NPCEC-Specific Expression in a Mammalian Host

Nucleic acids comprising an expressible sequence encoding a gene product of interest can be inserted into an expression vector comprising the NPCEC-specific promoter construct to create an expression cassette capable of producing the gene product of interest selectively in NPCECs in a mammalian host. Expression cassettes typically include control elements operably linked to the coding sequence, which allow for the expression of the gene in vivo in the subject species. For example, the expressible sequence of interest is operably linked to the minimal BEST2 promoter to allow mammalian expression. The ability of constructs to produce the gene product can be empirically determined.

Typically, transcription termination and polyadenylation sequences will also be present, located 3' to the translation stop codon. Preferably, a sequence for optimization of initiation of translation, located 5' to the coding sequence, is also present. Examples of transcription terminator/polyadenylation signals include those derived from SV40, as described in Sambrook et al., supra, as well as a bovine growth hormone terminator sequence.

Enhancer elements may also be used to increase expression levels of the mammalian constructs. Examples include the SV40 early gene enhancer, as described in Dijkema et al., *EMPO J.* (1985) 4:761, the enhancer/promoter derived from the long terminal repeat (LTR) of the Rous Sarcoma Virus, as described in Gorman et al., *Proc. Natl. Acad. Sci. USA* (1982b) 79:6777 and elements derived from human CMV, as described in Boshart et al., *Cell* (1985) 41:521, such as elements included in the CMV intron A sequence.

Additionally, 5'-UTR sequences can be placed adjacent to the coding sequence in order to enhance expression of the same. Such sequences may include UTRs comprising an internal ribosome entry site (IRES). Inclusion of an IRES permits the translation of one or more open reading frames from a vector. The IRES element attracts a eukaryotic ribosomal translation initiation complex and promotes translation initiation. See, e.g., Kaufman et al., *Nuc. Acids Res.* (1991) 19:4485-4490; Gurtu et al., *Biochem. Biophys. Res. Comm.* (1996) 229:295-298; Rees et al., *BioTechniques* (1996) 20:102-110; Kobayashi et al., *BioTechniques* (1996) 21:399-402; and Mosser et al., *BioTechniques* (1997) 22

150-161. A multitude of IRES sequences are known and include sequences derived from a wide variety of viruses, such as from leader sequences of picornaviruses such as the encephalomyocarditis virus (EMCV) UTR (Jang et al. *J. Virol.* (1989) 63:1651-1660), the polio leader sequence, the hepatitis A virus leader, the hepatitis C virus IRES, human rhinovirus type 2 IRES (Dobrikova et al., *Proc. Natl. Acad. Sci.* (2003) 100 (25): 15125-15130), an IRES element from the foot and mouth disease virus (Ramesh et al., *Nucl. Acid Res.* (1996) 24:2697-2700), a giardiavirus IRES (Garlapati et al., *J. Biol. Chem.* (2004) 279 (5): 3389-3397), and the like. A variety of nonviral IRES sequences will also find use herein, including, but not limited to IRES sequences from yeast, as well as the human angiotensin II type 1 receptor IRES (Martin et al., *Mol. Cell Endocrinol.* (2003) 212:51-61), fibroblast growth factor IRESs (FGF-1 IRES and FGF-2 IRES, Martineau et al. (2004) *Mol. Cell. Biol.* 24 (17): 7622-7635), vascular endothelial growth factor IRES (Baranick et al. (2008) *Proc. Natl. Acad. Sci. U.S.A.* 105 (12): 4733-4738, Stein et al. (1998) *Mol. Cell. Biol.* 18 (6): 3112-3119, Bert et al. (2006) RNA 12 (6): 1074-1083), and insulin-like growth factor 2 IRES (Pedersen et al. (2002) *Biochem. J.* 363 (Pt 1): 37-44). These elements are readily commercially available in plasmids sold, e.g., by Clontech (Mountain View, CA), Invivogen (San Diego, CA), Addgene (Cambridge, MA) and GeneCopoeia (Rockville, MD). See also IRESite: The database of experimentally verified IRES structures (iresite.org). An IRES sequence may be included in a vector, for example, to express multiple protein products in combination.

Alternatively, a polynucleotide encoding a viral T2A peptide can be used to allow production of multiple protein products from a single vector. 2A linker peptides are inserted between the coding sequences in the multicistronic construct. The 2A peptide, which is self-cleaving, allows co-expressed proteins from the multicistronic construct to be produced at equimolar levels. 2A peptides from various viruses may be used, including, but not limited to 2A peptides derived from the foot-and-mouth disease virus, equine rhinitis A virus, *Thosea asigna* virus and porcine teschovirus-1. See, e.g., Kim et al. (2011) *PLOS One* 6 (4): e18556, Trichas et al. (2008) *BMC Biol.* 6:40, Provost et al. (2007) *Genesis* 45 (10): 625-629, Furler et al. (2001) *Gene Ther.* 8 (11): 864-873; herein incorporated by reference in their entireties.

In certain embodiments, cells containing the NPCEC-specific promoter construct are identified in vitro or in vivo by including a selection marker expression cassette in the construct. Selection markers confer an identifiable change to the cell permitting positive selection of cells having the construct. For example, fluorescent or bioluminescent markers (e.g., green fluorescent protein (GFP), enhanced green fluorescent protein (EGFP), Dronpa, mCherry, mOrange, mPlum, Venus, YPet, phycoerythrin, or luciferase), cell surface markers, expression of a reporter gene (e.g., GFP, dsRed, GUS, lacZ, CAT), drug selection markers such as genes that confer resistance to neomycin, puromycin, hygromycin, DHFR, GPT, zeocin, or histidinol may be used to identify cells. Alternatively, enzymes such as herpes simplex virus thymidine kinase (tk) or chloramphenicol acetyltransferase (CAT) may be employed. Any selectable marker may be used as long as it is capable of being expressed in the cell to allow identification of genetically modified cells containing the construct. Further examples of selectable markers are well known to one of skill in the art.

In certain embodiments, the selection marker expression cassette encodes two or more selection markers. Selection markers may be used in combination, for example, a cell surface marker may be used with a fluorescent marker, or a drug resistance gene may be used with a suicide gene. In certain embodiments, the selection marker expression cassette is multicistronic to allow expression of multiple selection markers in combination. The multicistronic vector may include an IRES or viral 2A peptide to allow expression of more than one selection marker from a single vector.

In certain embodiments, a suicide marker is included as a negative selection marker to facilitate negative selection of cells. Suicide genes can be used to selectively kill cells by inducing apoptosis or converting a nontoxic drug to a toxic compound in genetically modified cells. Examples include suicide genes encoding thymidine kinases, cytosine deaminases, intracellular antibodies, telomerases, caspases, and DNases. In certain embodiments, a suicide gene is used in combination with one or more other selection markers, such as those described above for use in positive selection of cells. In addition, a suicide gene may be used in genetically modified cells, for example, to improve their safety by allowing their destruction at will. See, e.g., Jones et al. (2014) Front. Pharmacol. 5:254, Mitsui et al. (2017) Mol. Ther. Methods Clin. Dev. 5:51-58, Greco et al. (2015) Front. Pharmacol. 6:95; herein incorporated by reference.

Once complete, the construct encoding a gene product of interest can be administered to a subject using standard gene delivery protocols. Methods for gene delivery are known in the art. See, e.g., U.S. Pat. Nos. 5,399,346, 5,580,859, 5,589,466. Genes can be delivered either directly to a vertebrate subject or, alternatively, delivered ex vivo, to cells derived from the subject and the cells reimplanted in the subject.

A number of viral based systems have been developed for gene transfer into mammalian cells. These include adenoviruses, retroviruses (γ-retroviruses and lentiviruses), poxviruses, adeno-associated viruses, baculoviruses, and herpes simplex viruses (see e.g., Warnock et al. (2011) *Methods Mol. Biol.* 737:1-25; Walther et al. (2000) *Drugs* 60 (2): 249-271; and Lundstrom (2003) *Trends Biotechnol.* 21 (3): 117-122; herein incorporated by reference).

For example, retroviruses provide a convenient platform for gene delivery systems. Selected sequences can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219,740; Miller and Rosman (1989) *BioTechniques* 7:980-990; Miller, A. D. (1990) *Human Gene Therapy* 1:5-14; Scarpa et al. (1991) *Virology* 180:849-852; Burns et al. (1993) *Proc. Natl. Acad. Sci. USA* 90:8033-8037; Boris-Lawrie and Temin (1993) *Cur. Opin. Genet. Develop.* 3:102-109; and Ferry et al. (2011) *Curr Pharm Des.* 17 (24): 2516-2527). Lentiviruses are a class of retroviruses that are particularly useful for delivering polynucleotides to mammalian cells because they are able to infect both dividing and nondividing cells (see e.g., Lois et al (2002) *Science* 295:868-872; Durand et al. (2011) *Viruses* 3 (2): 132-159; herein incorporated by reference).

A number of adenovirus vectors have also been described. Unlike retroviruses which integrate into the host genome, adenoviruses persist extrachromosomally thus minimizing the risks associated with insertional mutagenesis (Haj-Ahmad and Graham, *J. Virol.* (1986) 57:267-274; Bett et al., *J. Virol.* (1993) 67:5911-5921; Mittereder et al., *Human Gene Therapy* (1994) 5:717-729; Seth et al., *J. Virol.* (1994) 68:933-940; Barr et al., *Gene Therapy* (1994) 1:51-58;

Berkner, K. L. *BioTechniques* (1988) 6:616-629; and Rich et al., *Human Gene Therapy* (1993) 4:461-476). Additionally, various adeno-associated virus (AAV) vector systems have been developed for gene delivery. AAV vectors can be readily constructed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al., *Molec. Cell. Biol.* (1988) 8:3988-3996; Vincent et al., *Vaccines* 90 (1990) (Cold Spring Harbor Laboratory Press); Carter, B. *J. Current Opinion in Biotechnology* (1992) 3:533-539; Muzyczka, N. *Current Topics in Microbiol. and Immunol.* (1992) 158:97-129; Kotin, R. M. *Human Gene Therapy* (1994) 5:793-801; Shelling and Smith, *Gene Therapy* (1994) 1:165-169; and Zhou et al., *J. Exp. Med.* (1994) 179:1867-1875.

Another vector system useful for delivering constructs of the present invention is the enterically administered recombinant poxvirus vaccines described by Small, Jr., P. A., et al. (U.S. Pat. No. 5,676,950, issued Oct. 14, 1997, herein incorporated by reference).

Additional viral vectors, which will find use for delivering constructs, comprising an expressible sequence of interest operably linked to the BEST2 minimal promoter, include those derived from the pox family of viruses, including vaccinia virus and avian poxvirus. By way of example, vaccinia virus recombinants expressing a gene product of interest can be constructed as follows. The expressible sequence encoding the particular gene product is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the coding sequences of interest into the viral genome. The resulting TK-recombinant can be selected by culturing the cells in the presence of 5-bromodeoxyuridine and picking viral plaques resistant thereto.

Alternatively, avipoxviruses, such as the fowlpox and canarypox viruses, can also be used to deliver the constructs. The use of an avipox vector is particularly desirable in human and other mammalian species since members of the avipox genus can only productively replicate in susceptible avian species and therefore are not infective in mammalian cells. Methods for producing recombinant avipoxviruses are known in the art and employ genetic recombination, as described above with respect to the production of vaccinia viruses. See, e.g., WO 91/12882; WO 89/03429; and WO 92/03545.

Molecular conjugate vectors, such as the adenovirus chimeric vectors described in Michael et al., *J. Biol. Chem.* (1993) 268:6866-6869 and Wagner et al., *Proc. Natl. Acad. Sci. USA* (1992) 89:6099-6103, can also be used for gene delivery.

Members of the Alphavirus genus, such as, but not limited to, vectors derived from the Sindbis virus (SIN), Semliki Forest virus (SFV), and Venezuelan Equine Encephalitis virus (VEE), will also find use as viral vectors for delivering the constructs. For a description of Sindbis-virus derived vectors useful for the practice of the instant methods, see, Dubensky et al. (1996) *J. Virol.* 70:508-519; and International Publication Nos. WO 95/07995, WO 96/17072; as well as, Dubensky, Jr., T. W., et al., U.S. Pat. No. 5,843,723, issued Dec. 1, 1998, and Dubensky, Jr., T. W., U.S. Pat. No. 5,789,245, issued Aug. 4, 1998, both herein incorporated by reference. Particularly preferred are chimeric alphavirus vectors comprised of sequences derived from Sindbis virus and Venezuelan equine encephalitis virus. See, e.g., Perri et al. (2003) *J. Virol.* 77:10394-10403 and International Publication Nos. WO 02/099035, WO 02/080982, WO 01/81609, and WO 00/61772; herein incorporated by reference in their entireties.

A synthetic expression cassette comprising the minimal BEST2 promoter operably linked to an expressible sequence of interest can also be delivered without a viral vector. For example, the synthetic expression cassette can be packaged as DNA or RNA in liposomes prior to delivery to the subject or to cells derived therefrom. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, Hug and Sleight, *Biochim. Biophys. Acta.* (1991.) 1097:1-17; Straubinger et al., *Methods of Enzymology* (1983), Vol. 101, pp. 512-527.

Liposomal preparations for use in the present invention include cationic (positively charged), anionic (negatively charged) and neutral preparations, with cationic liposomes particularly preferred. Cationic liposomes have been shown to mediate intracellular delivery of plasmid DNA (Felgner et al., *Proc. Natl. Acad. Sci. USA* (1987) 84:7413-7416); mRNA (Malone et al., *Proc. Natl. Acad. Sci. USA* (1989) 86:6077-6081); and purified transcription factors (Debs et al., *J. Biol. Chem.* (1990) 265:10189-10192), in functional form.

Cationic liposomes are readily available. For example, N [1-2,3-dioleyloxy) propyl]-N,N,N-triethylammonium (DOTMA) liposomes are available under the trademark Lipofectin, from GIBCO BRL, Grand Island, N.Y. (See, also, Felgner et al., *Proc. Natl. Acad. Sci. USA* (1987) 84:7413-7416). Other commercially available lipids include (DDAB/DOPE) and DOTAP/DOPE (Boerhinger). Other cationic liposomes can be prepared from readily available materials using techniques well known in the art. See, e.g., Szoka et al., *Proc. Natl. Acad. Sci. USA* (1978) 75:4194-4198; PCT Publication No. WO 90/11092 for a description of the synthesis of DOTAP (1,2-bis(oleoyloxy)-3-(trimethylammonio) propane) liposomes.

Similarly, anionic and neutral liposomes are readily available, such as, from Avanti Polar Lipids (Birmingham, AL), or can be easily prepared using readily available materials. Such materials include cholesterol, phosphatidyl choline, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See, e.g., Straubinger et al., in METHODS OF IMMUNOLOGY (1983), Vol. 101, pp. 512-527; Szoka et al., *Proc. Natl. Acad. Sci. USA* (1978) 75:4194-4198; Papahadjopoulos et al., *Biochim. Biophys. Acta* (1975) 394:483; Wilson et al., Cell (1979) 17:77); Deamer and Bangham, *Biochim. Biophys. Acta* (1976) 443:629; Ostro et al., *Biochem. Biophys. Res. Commun.* (1977) 76:836; Fraley et al., *Proc. Natl. Acad. Sci. USA* (1979) 76:3348); Enoch and Strittmatter, *Proc. Natl. Acad. Sci. USA* (1979) 76:145); Fraley et al., *J. Biol.*

*Chem.* (1980) 255:10431; Szoka and Papahadjopoulos, *Proc. Natl. Acad. Sci. USA* (1978) 75:145; and Schaefer-Ridder et al., *Science* (1982) 215:166.

The DNA and/or peptide(s) can also be delivered in cochleate lipid compositions similar to those described by Papahadjopoulos et al., *Biochem. Biophys. Acta.* (1975) 394:483-491. See, also, U.S. Pat. Nos. 4,663,161 and 4,871, 488.

The expression cassette comprising the minimal BEST2 promoter operably linked to an expressible sequence of interest may also be encapsulated, adsorbed to, or associated with, particulate carriers. Examples of particulate carriers include those derived from polymethyl methacrylate polymers, as well as microparticles derived from poly(lactides) and poly(lactide-co-glycolides), known as PLG. See, e.g., Jeffery et al., *Pharm. Res.* (1993) 10:362-368; McGee J. P., et al., *J. Microencapsul.* 14 (2): 197-210, 1997; O'Hagan D. T., et al., *Vaccine* 11 (2): 149-54, 1993.

Furthermore, other particulate systems and polymers can be used for the in vivo or ex vivo delivery of a nucleic acid of interest. For example, polymers such as polylysine, polyarginine, polyornithine, spermine, spermidine, as well as conjugates of these molecules, are useful for transferring a nucleic acid of interest. Similarly, DEAE dextran-mediated transfection, calcium phosphate precipitation or precipitation using other insoluble inorganic salts, such as strontium phosphate, aluminum silicates including bentonite and kaolin, chromic oxide, magnesium silicate, talc, and the like, will find use with the present methods. See, e.g., Felgner, P. L., *Advanced Drug Delivery Reviews* (1990) 5:163-187, for a review of delivery systems useful for gene transfer. Peptoids (Zuckerman, R. N., et al., U.S. Pat. No. 5,831,005, issued Nov. 3, 1998, herein incorporated by reference) may also be used for delivery of a construct of the present invention.

Additionally, biolistic delivery systems employing particulate carriers such as gold and tungsten, are especially useful for delivering a synthetic expression cassette comprising the minimal BEST2 promoter operably linked to an expressible sequence of interest. The particles are coated with the synthetic expression cassette(s) to be delivered and accelerated to high velocity, generally under a reduced atmosphere, using a gun powder discharge from a "gene gun." For a description of such techniques, and apparatuses useful therefore, see, e.g., U.S. Pat. Nos. 4,945,050; 5,036, 006; 5,100,792; 5,179,022; 5,371,015; and 5,478,744. Also, needle-less injection systems can be used (Davis, H. L., et al, Vaccine 12:1503-1509, 1994; Bioject, Inc., Portland, Oreg.).

In some embodiments, recombinant vectors carrying an expression cassette comprising the minimal BEST2 promoter operably linked to an expressible sequence of interest are used in gene therapy applications to treat an eye disease. The vectors can be formulated into compositions for delivery to a vertebrate subject (e.g., mammalian subject, preferably human). These compositions may either be prophylactic (to prevent a disease or condition) or therapeutic (to treat a disease or condition). The compositions will comprise a "therapeutically effective amount" of the nucleic acid of interest such that amounts of the gene product of interest can be produced in vivo sufficient to have a therapeutic benefit in the individual to which it is administered. The exact amounts necessary will vary depending on the subject being treated; the age and general condition of the subject to be treated; the degree of protection desired; the severity of the condition being treated; the particular therapeutic agent produced, and the mode of administration, among other factors. An appropriate effective amount can be readily determined by one of skill in the art. Thus, a "therapeutically effective amount" will fall in a relatively broad range that can be determined through routine trials.

The compositions will generally include one or more "pharmaceutically acceptable excipients or vehicles" such as water, saline, glycerol, polyethyleneglycol, hyaluronic acid, ethanol, etc. Additionally, auxiliary substances, such as wetting or emulsifying agents, pH buffering substances, surfactants and the like, may be present in such vehicles. Certain facilitators of nucleic acid uptake and/or expression can also be included in the compositions or coadministered.

Once formulated, the compositions can be administered directly to the subject (e.g., as described above) or, alternatively, delivered ex vivo, to cells derived from the subject, using methods such as those described above. For example, methods for the ex vivo delivery and reimplantation of transformed cells into a subject are known in the art and can include, e.g., dextran-mediated transfection, calcium phosphate precipitation, polybrene mediated transfection, lipofectamine and LT-1 mediated transfection, protoplast fusion, electroporation, encapsulation of the polynucleotide(s) in liposomes, and direct microinjection of the DNA into nuclei.

Direct delivery of expression cassette compositions comprising the NPCEC-specific promoter operably linked to an expressible sequence of interest in vivo will generally be accomplished with or without viral vectors, as described above, by injection using either a conventional syringe, needless devices such as Bioject or a gene gun, such as the Accell gene delivery system (PowderMed Ltd, Oxford, England).

Kits

Also provided are kits for use in expressing a gene product of interest specifically in NPCECs. In some embodiments, the kit provides a construct comprising a minimal BEST2 promoter and a transcriptional start site (TSS), as described therein, or an expression cassette or expression vector comprising such a construct. Other agents may also be included in the kit such as transfection agents, NPCECs, suitable media for culturing NPCECs, buffers, and the like.

In some embodiments, the kit comprises a construct comprising a minimal BEST2 promoter nucleotide sequence selected from the group consisting of SEQ ID NO:1 and SEQ ID NO: 2; or sequences displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto In the context of a kit, any of these agents can be provided in liquid or sold form in any convenient packaging (e.g., stick pack, dose pack, etc.). The agents of a kit can be present in the same or separate containers. The agents may also be present in the same container. In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

In Vitro Targeting of Non-Pigmented Ciliary Epithelial Cells

The ciliary body not only plays a key role in eye disease (i.e. glaucoma) but also contains many other possible therapeutic targets, such as adrenergic alpha and beta receptors, dopamine receptors, prostaglandin receptors and peptide receptors. FIG. 1 shows a schematic of the location of the ciliary body within the human eye. The ciliary body allows for the continual secretion of aqueous humor and the control of intraocular pressure (IOP). It is highly vascularized, and the non-pigmented ciliary epithelial cells (NPCECs) act as a barrier.

Figure 2A:
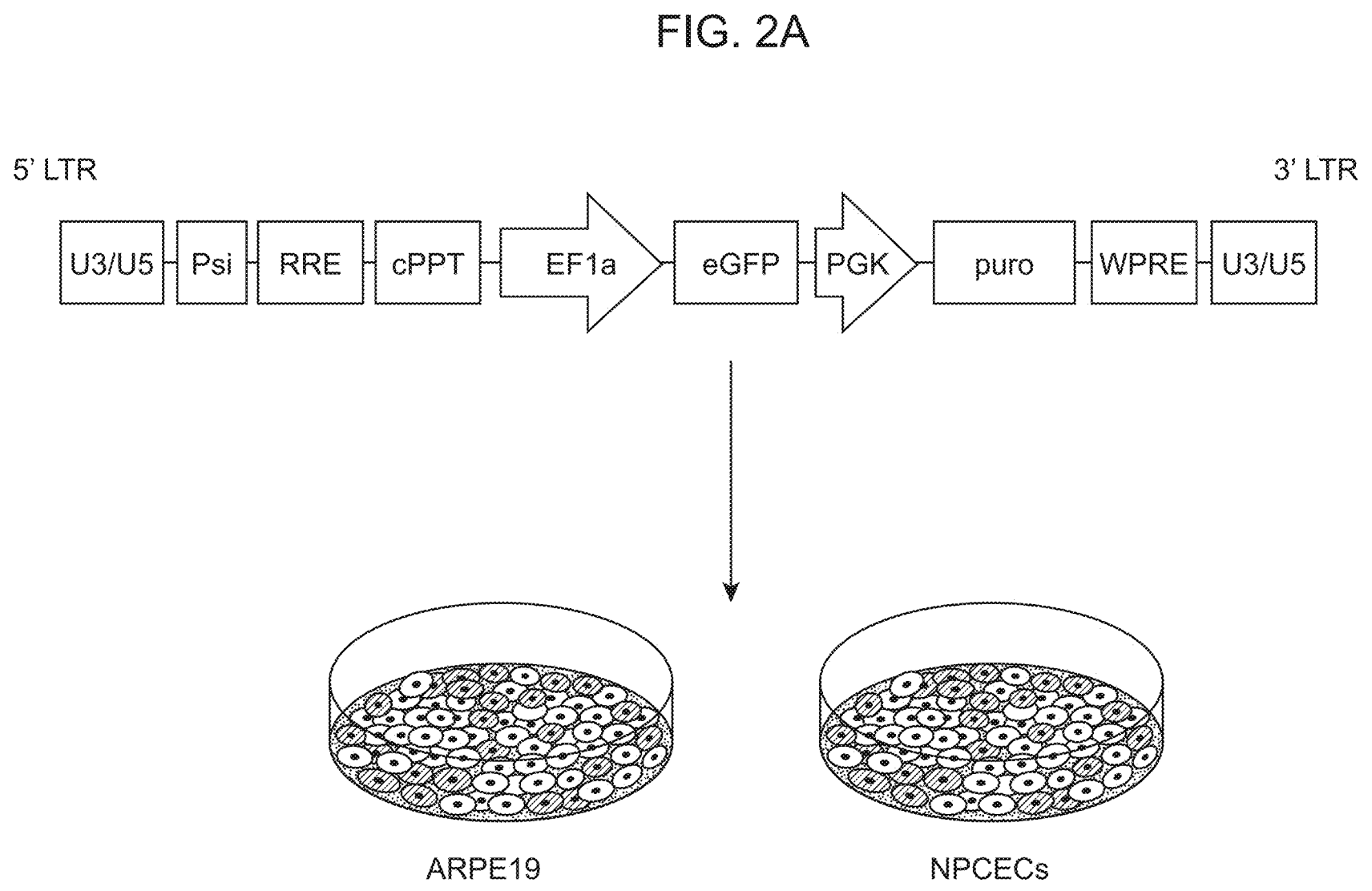
Figure 2B:
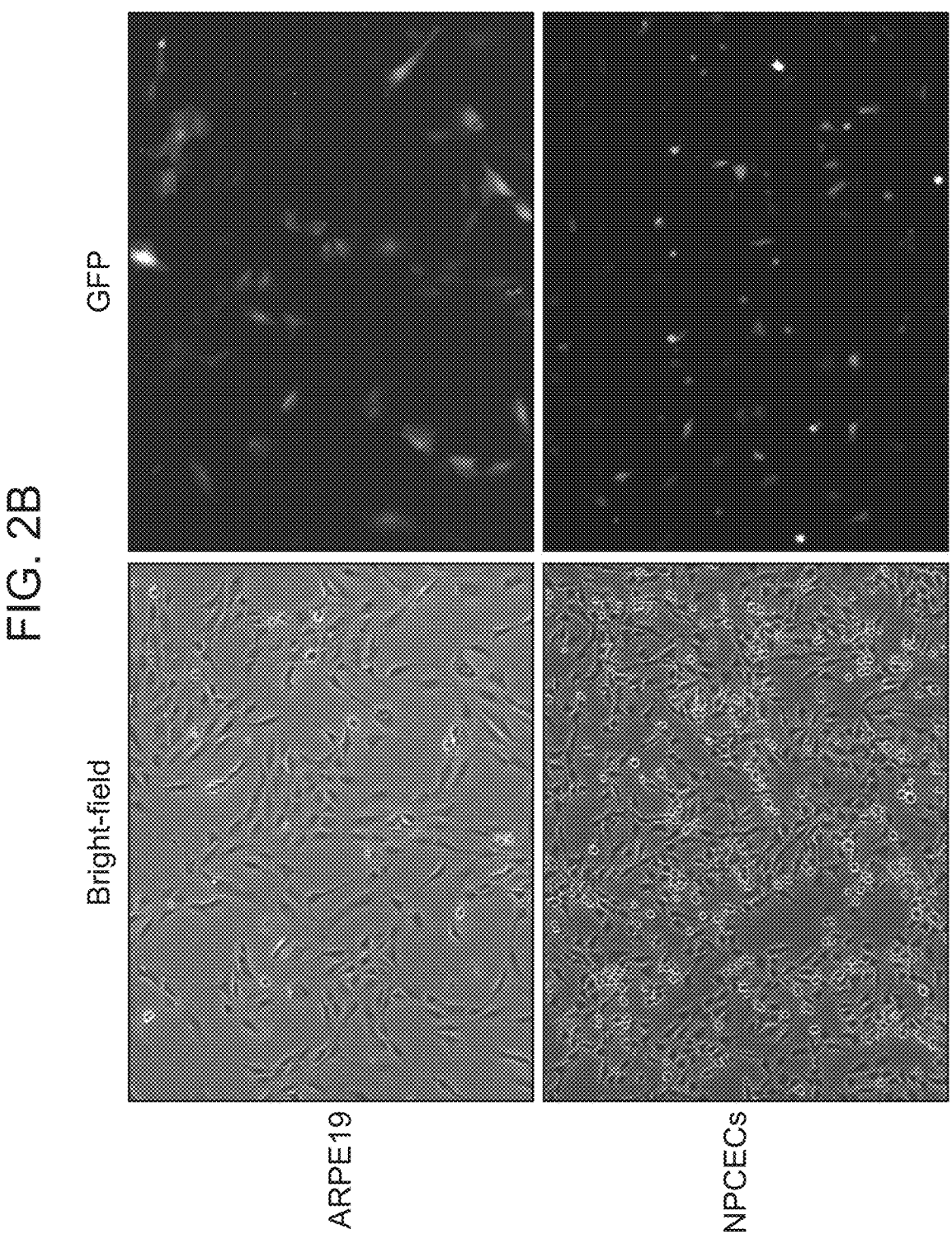
Figure 2C:
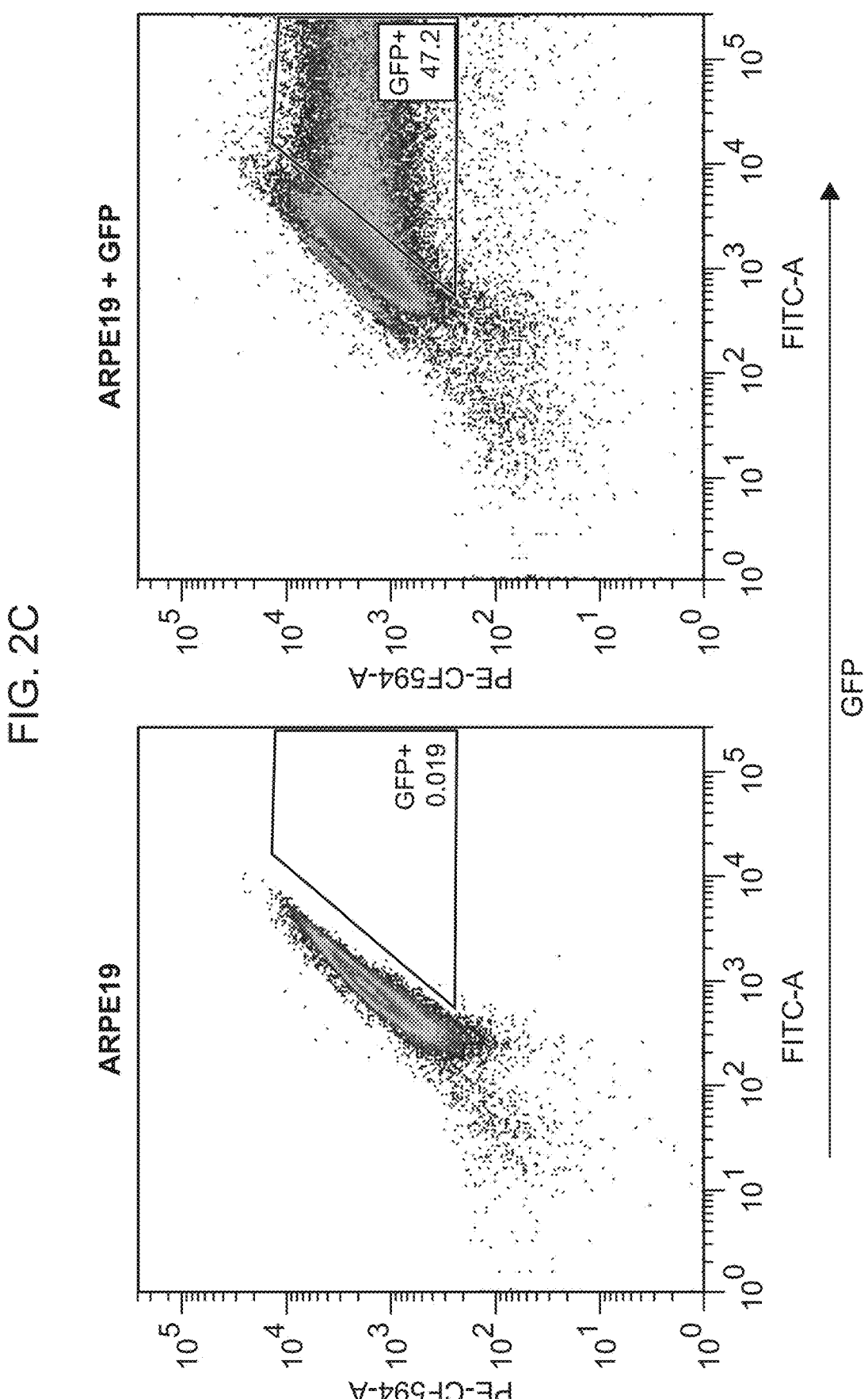
Figure 2C:
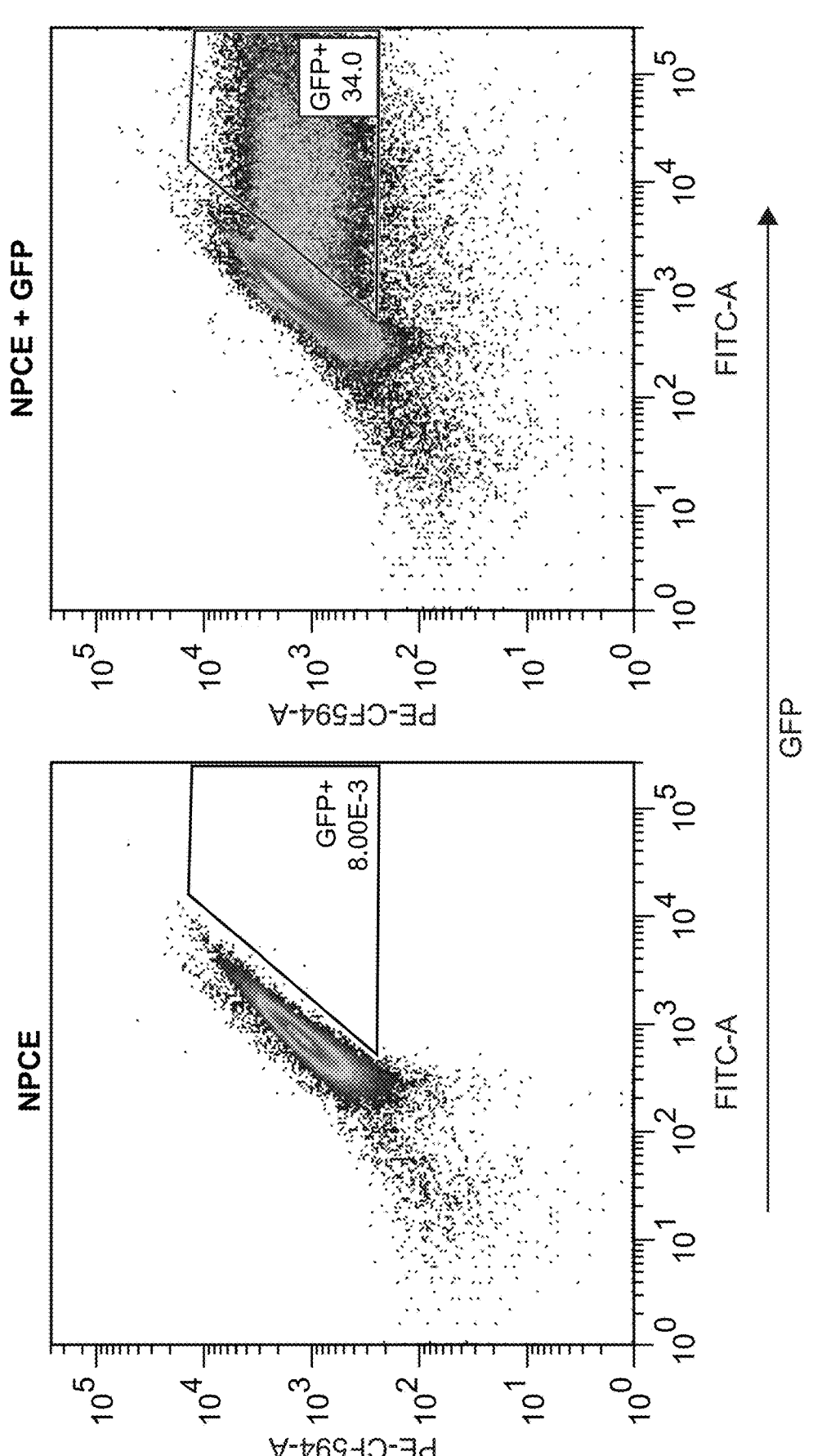

A human retinal pigment epithelial cell line (ARPE19) and human non-pigmented ciliary epithelial cells (NPCECs) were transfected with a lentiviral construct containing a green fluorescent protein (GFP) driven by the constitutively active EF1a (elongation factor 1 alpha) promoter, LTR, long-terminal repeat; U3/U5, unique 3' or 5' region; Psi, RNA target site for packaging by nucleocapsid; RRE, Rev Response Element; cPPT, Central polypurine tract; PGK, phosphoglycerate kinase promoter; Puro, puromycin resistance gene; WPRE, and Woodchuck hepatitis virus post-transcriptional regulatory element (FIG. 2A). GFP was detectable via fluorescence microscopy 24 hours post-transfection in both ARPE19 and NPCE cells at 5× magnification (FIG. 2B). FACs sorting showed an approximate 35% transfection efficiency of the lentiviral construct in both ARPE19 and NPCE cells (FIG. 2C).

Example 2

Figure 3:
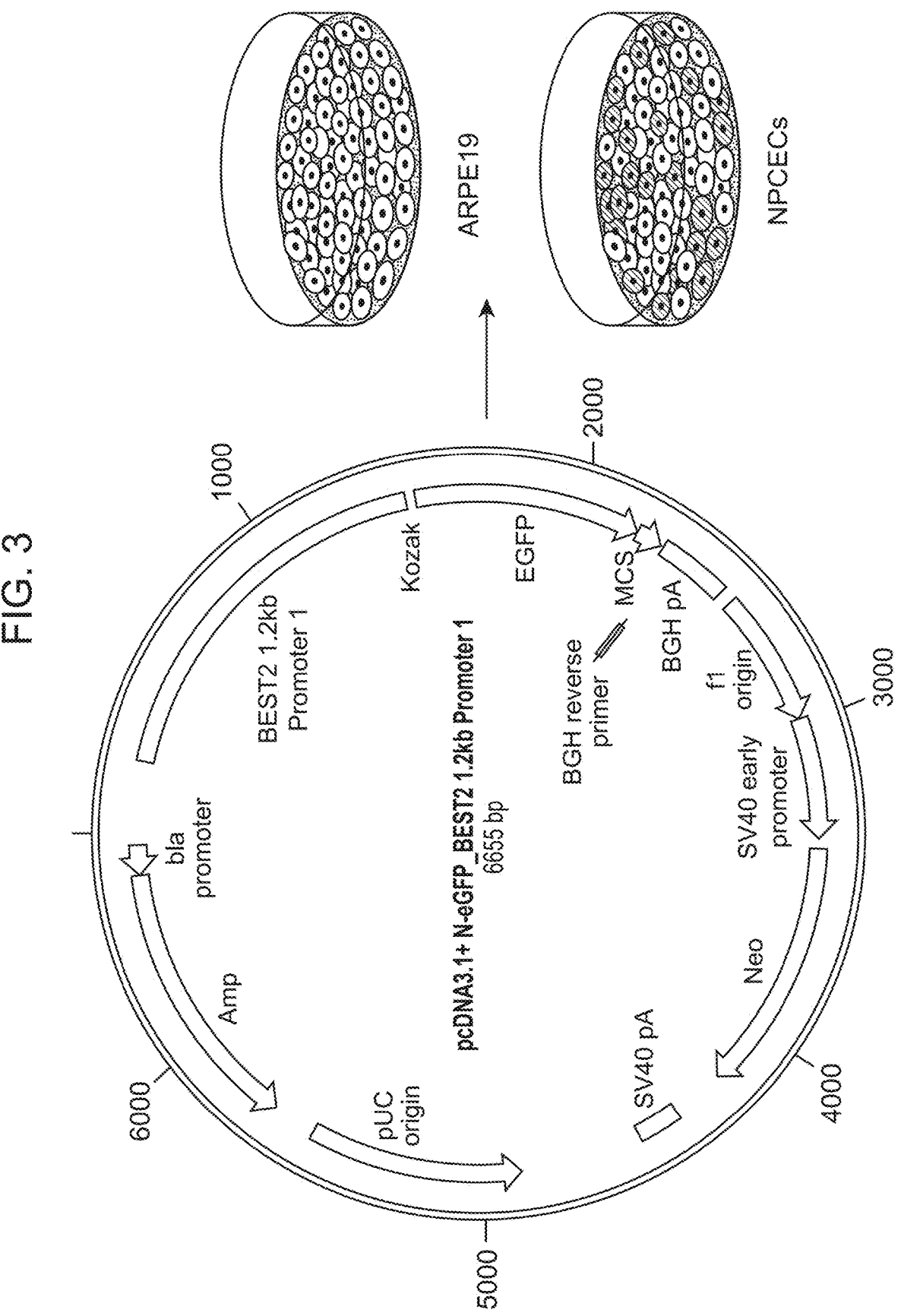
FIG. 3 shows VMD2L1 preferential targeting of non-pigmented ciliary epithelial cells. Strategy to determine a promoter sequence specific to the non-pigmented ciliary epithelial cells (NPCECs) of the eye. BEST2 is a gene specific to the NPCECs and no other epithelial cells, such as the RPE cells in the eye. There are no specific predictor sites for the BEST2 promoter, although the region upstream of the BEST2 gene is a suggested location for the promoter sequence. A human retinal pigment epithelial cell line (ARPE19) and human non-pigmented ciliary epithelial cells (NPCECs) were transfected with a plasmid construct containing green fluorescent protein (GFP) driven by a sequence (chr19:12,750,691-12,751,903) approximately 1.1 kb upstream of the BEST2 gene (chr19:12,751,702-12,758, 458), with some overlap into the gene itself. If this upstream region contains the promoter for BEST2, GFP should be expressed in the NPCE and not the ARPE19 cells. MCS, multiple cloning site; BGH pA, bovine growth hormone poly A; SV40, simian virus 40; Neo, neomycin resistance gene; Amp, ampicilin resistance gene.

Identifying a Promoter Sequence Specific for Non-Pigmented Ciliary Epithelial Cells The BEST2 gene is specifically expressed in NPCECs and not in other epithelial cells, such as the RPE cells in the eye. Although there are no specific predictor sites for the BEST2 promoter, the region upstream of the BEST2 gene is a suggested location for the promoter sequence. A human retinal pigment epithelial cell line (ARPE19) and human non-pigmented ciliary epithelial cells (NPCECs) were transfected with a plasmid construct containing green fluorescent protein (GFP) driven by a sequence (chr19:12,750,691-12, 751,903) approximately 1.1 kb upstream of the BEST2 gene (chr19:12,751,702-12,758,458), with some overlap into the gene itself. If this upstream region contained the promoter for BEST2, GFP should be expressed in the NPCEs and not the ARPE19 cells. A schematic of the plasmid is shown in FIG. 3. The plasmid contains a multiple cloning site (MCS), a bovine growth hormone polyadenylation (BGH pA) sequence, a simian virus 40 (SV40) early promoter, a neomycin resistance gene (Neo) selection marker, and an ampicillin resistance gene (Amp) selection marker.

Figure 4A:
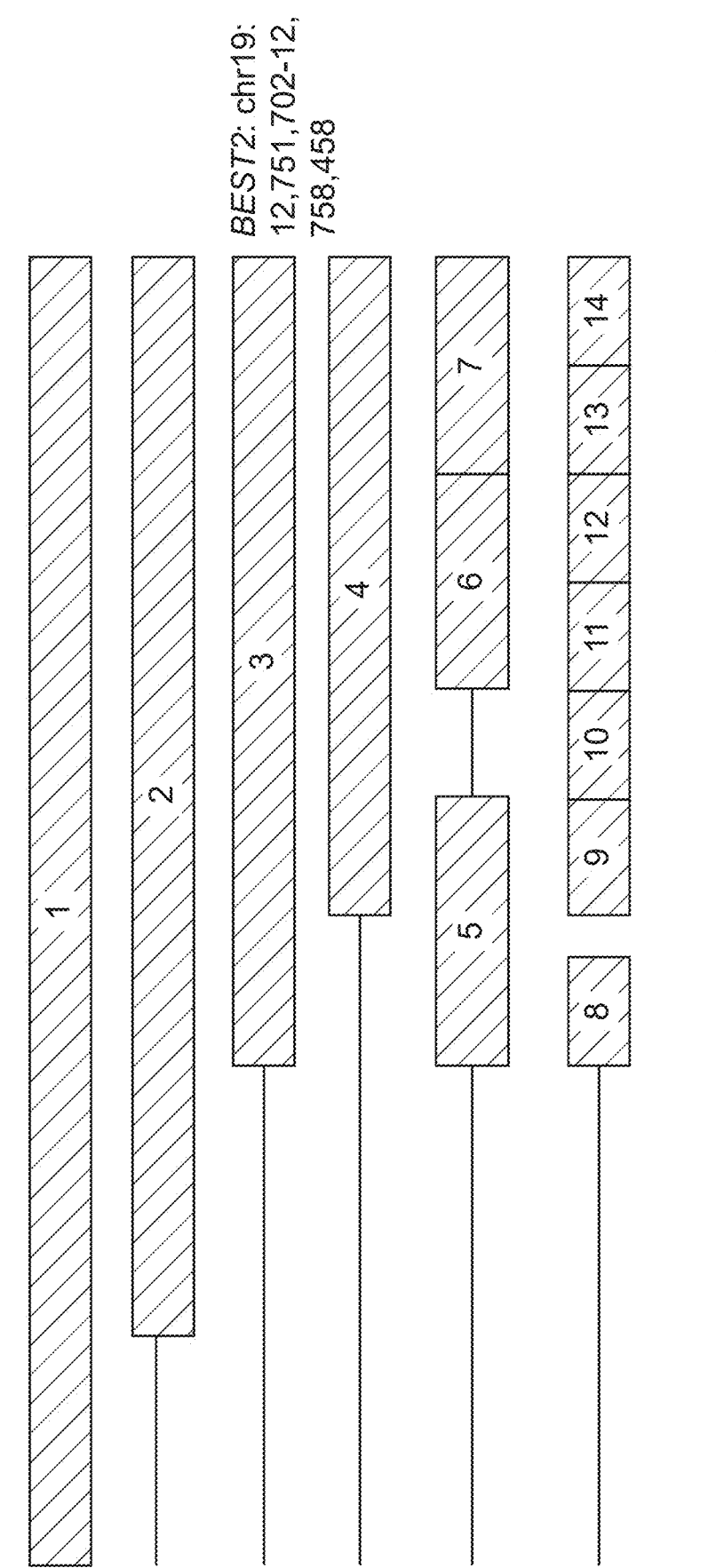
Figure 4B:
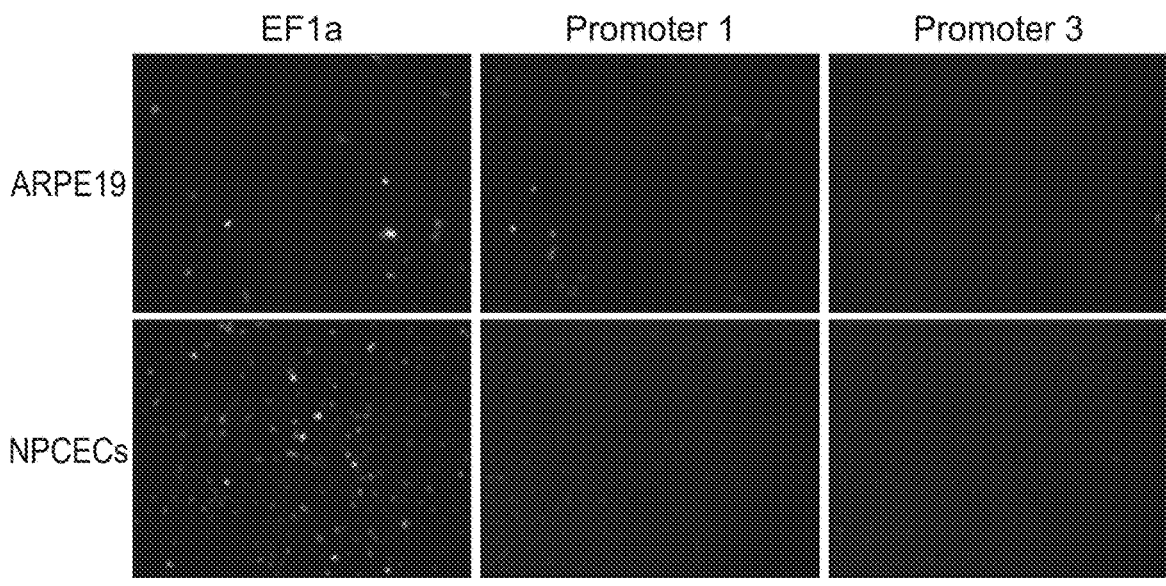
Figure 4B:
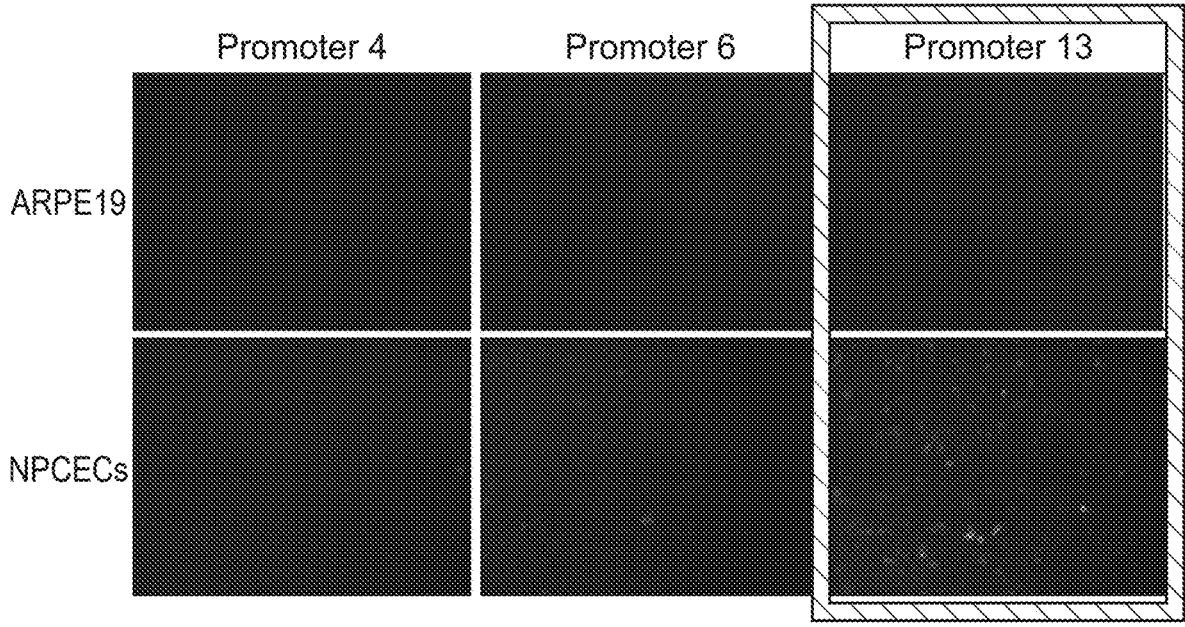
Figure 4C:
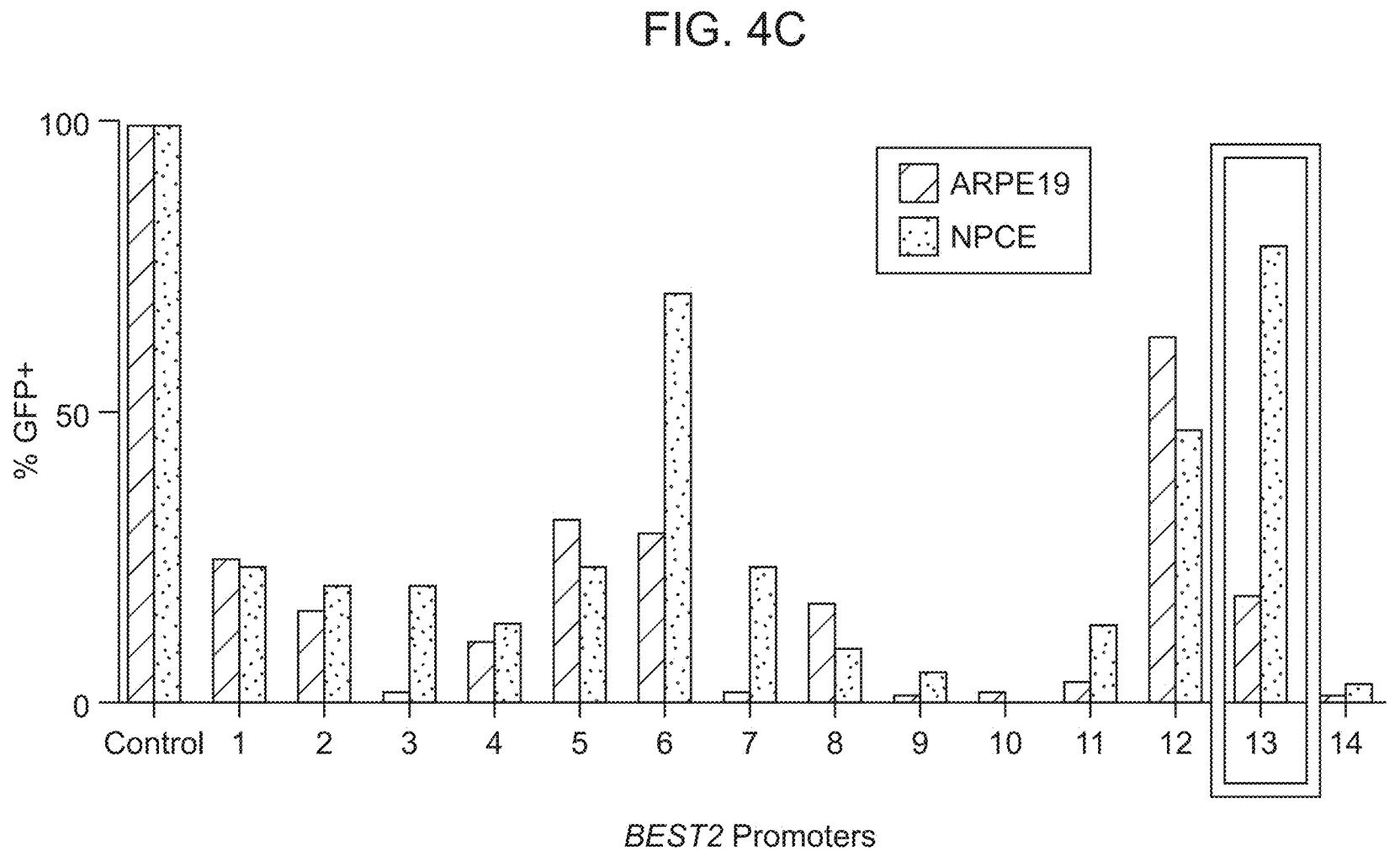

Next, the size of the upstream region presumed to contain the promoter for BEST2 was reduced to determine the promoter sequence driving preferential targeting of non-pigmented ciliary epithelial cells. A plasmid construct was created containing green fluorescent protein (GFP) driven by the constitutively active EF1a (elongation factor 1 alpha) promoter, the sequence (promoter 1; chr19:12,750,691-12, 751,903) approximately 1.1 kb upstream of the BEST2 gene (chr19:12,751,702-12,758,458), and shortened versions down to 100 bp of this upstream region (promoters 2-14). A human retinal pigment epithelial cell line (ARPE19) and human non-pigmented ciliary epithelial cells (NPCECs) were transfected with a plasmid construct containing green fluorescent protein (GFP) driven by each of the promoters shown in the FIG. 4A (EF1a and promoters 1-14). Representative images of GFP positive cells are shown in FIG. 4B for the EF1a promoter (control) and promoters 1, 3, 4, 6, and 13 approximately 24 hours after transfection. FACs sorting was used to determine the percent of GFP positive ARPE19 or NPCE cells after transfection with promoters 1-14, normalized to the EF1a controls for each cell line. Promoter 13 (100 bp sequence of SEQ ID NO:1) showed a specificity for NPCE cells over ARPE19 cells (FIG. 4C).

Example 3

Exclusion of Additional Predicted Promoter Regions for VMD2L1

Figure 5A:
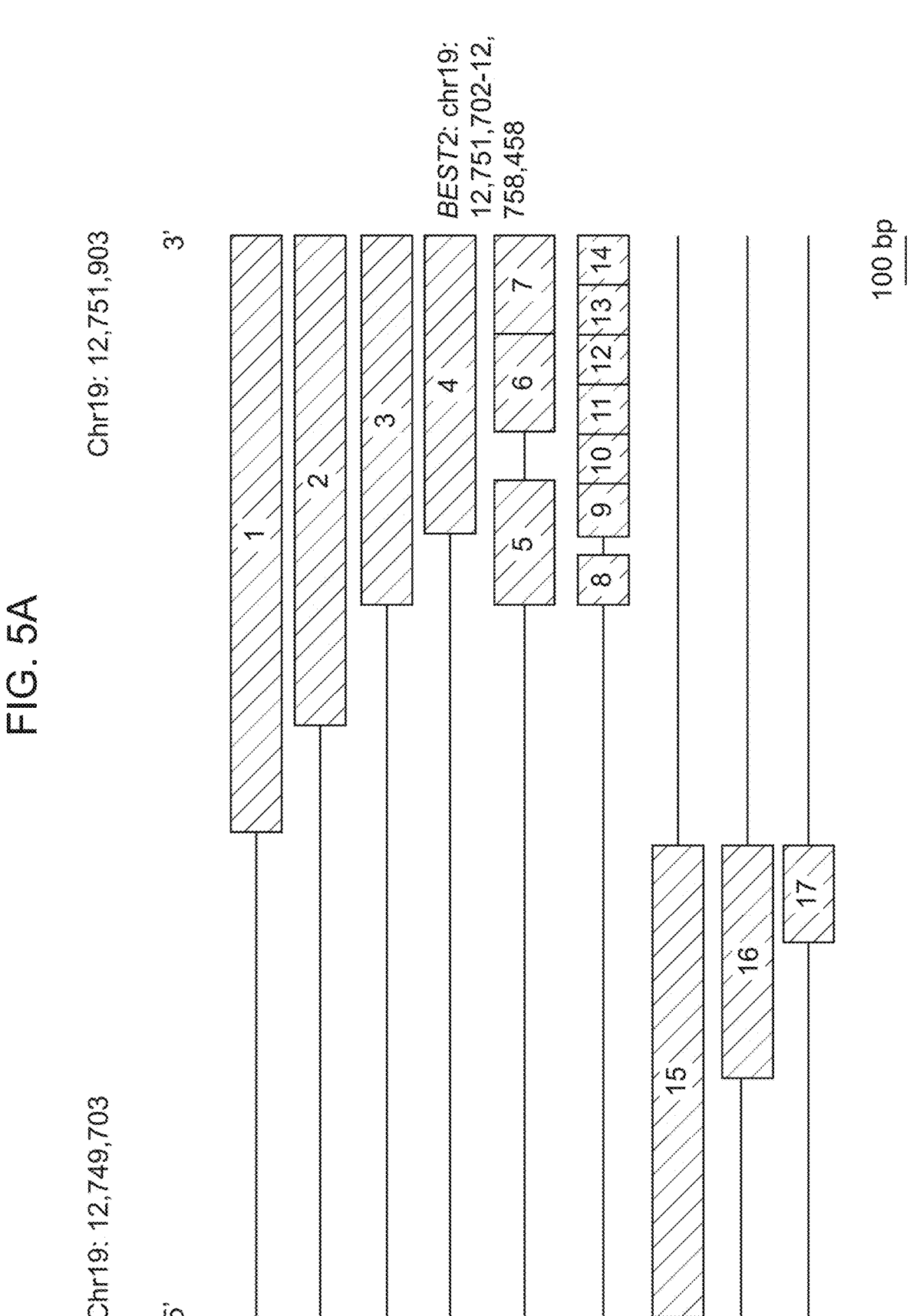
FIGS. 5A-5B show exclusion of additional predicted promoter regions for VMD2L1.
Figure 5B:
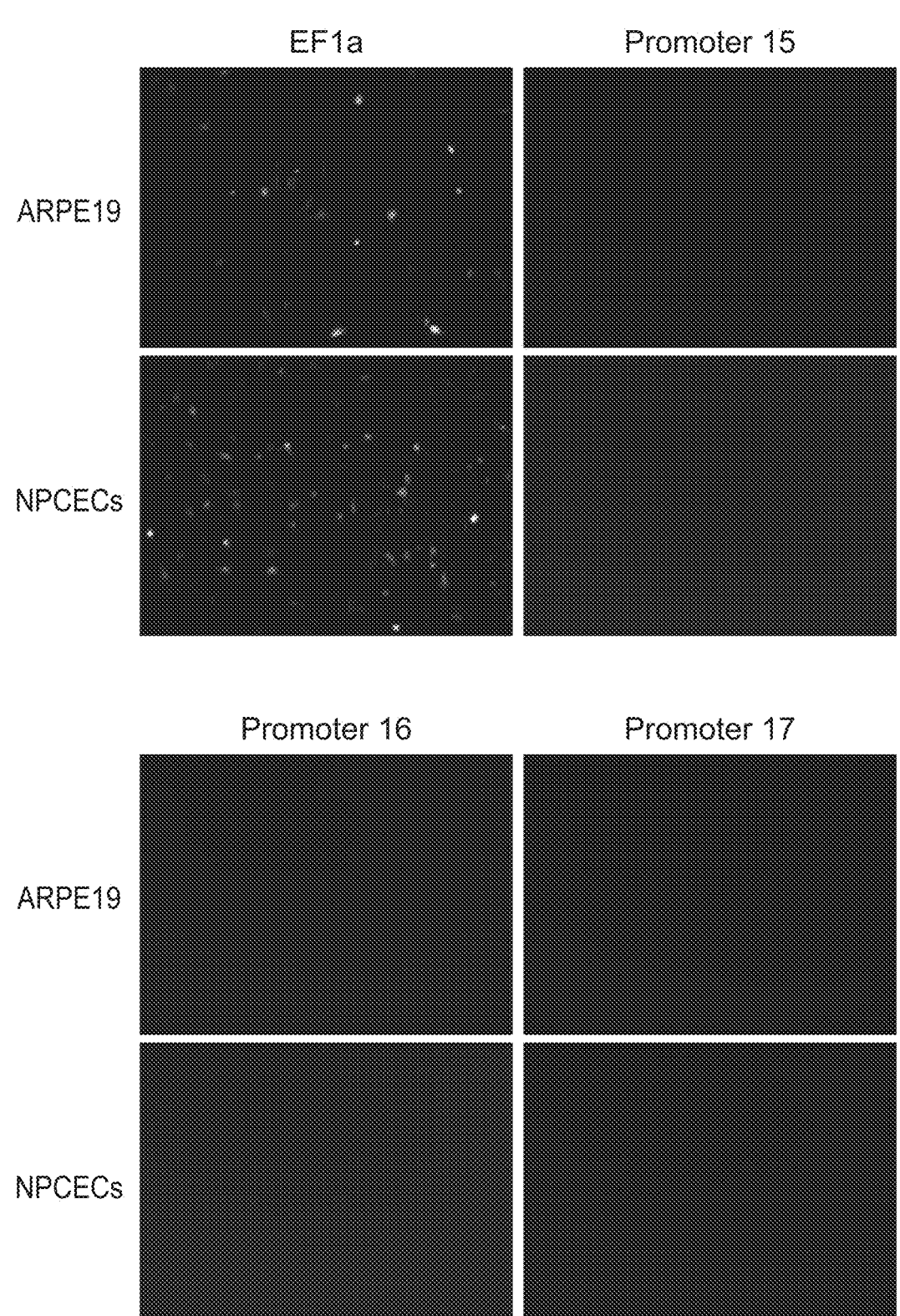

Three additional promoter sequences (promoters 15-17; chr19:12,749,703-12,750,691) were designed upstream of promoter 1, in a second region suggested to contain a potential promoter for the BEST2 gene (FIG. 5A). A human retinal pigmented epithelial cell line (ARPE19) and human non-pigmented ciliary epithelial cells (NPCECs) were transfected with a plasmid construct containing green fluorescent protein (GFP) driven by promoters 15-17 (shown in FIG. 5A), which were compared to EF1a controls. FIG. 5B shows representative images of GFP positive cells for the EF1a promoter (control) and promoters 15-17 at approximately 24 hours after transfection. No GFP was detectable for plasmids containing promoters 15-17.

Example 4

Transcription Factors Binding at Promoter Regions of VMD2L1

Figure 6A:
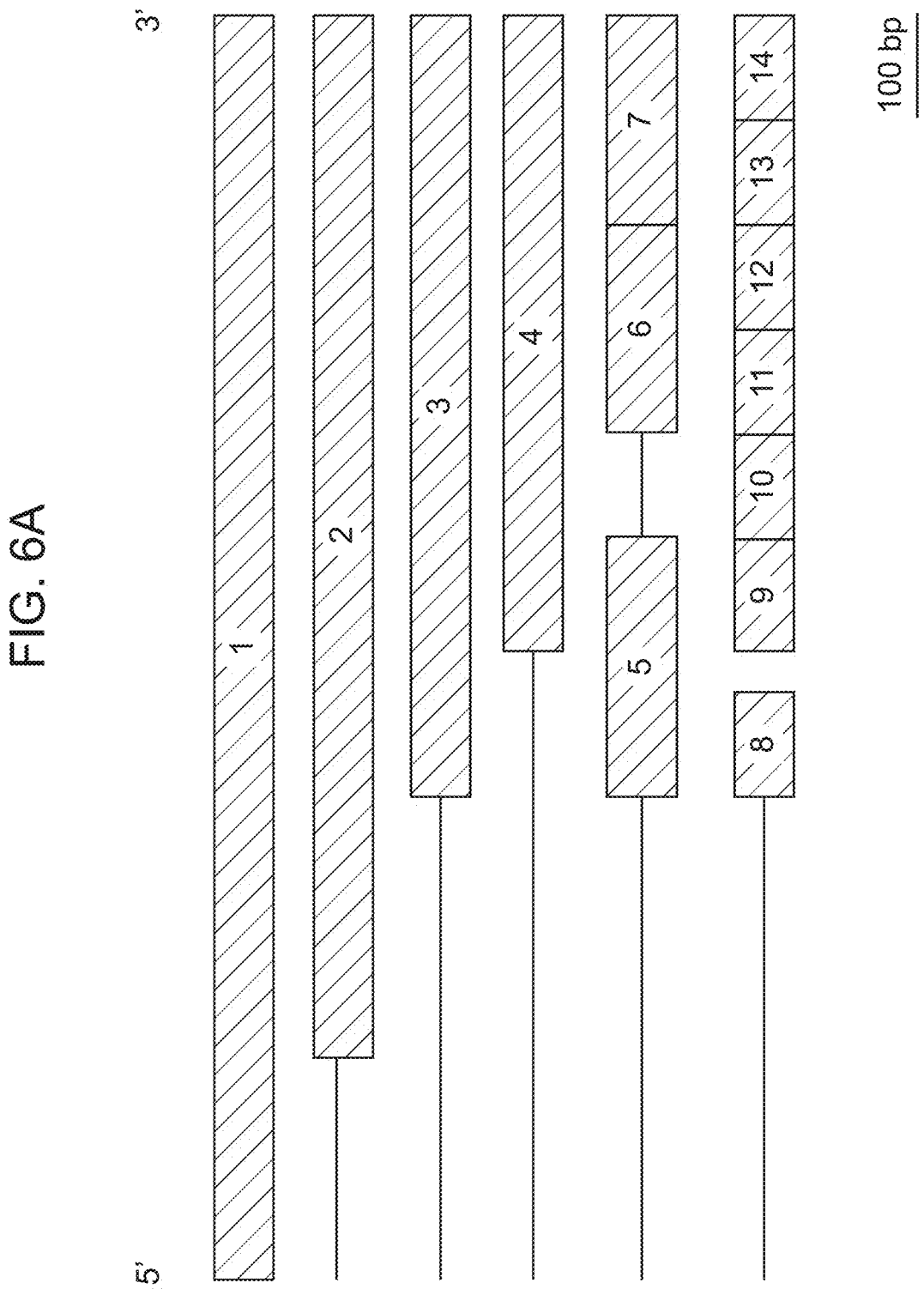
FIGS. 6A-6C show transcription factors binding at promoter regions of VMD2L1.
Figure 6B:
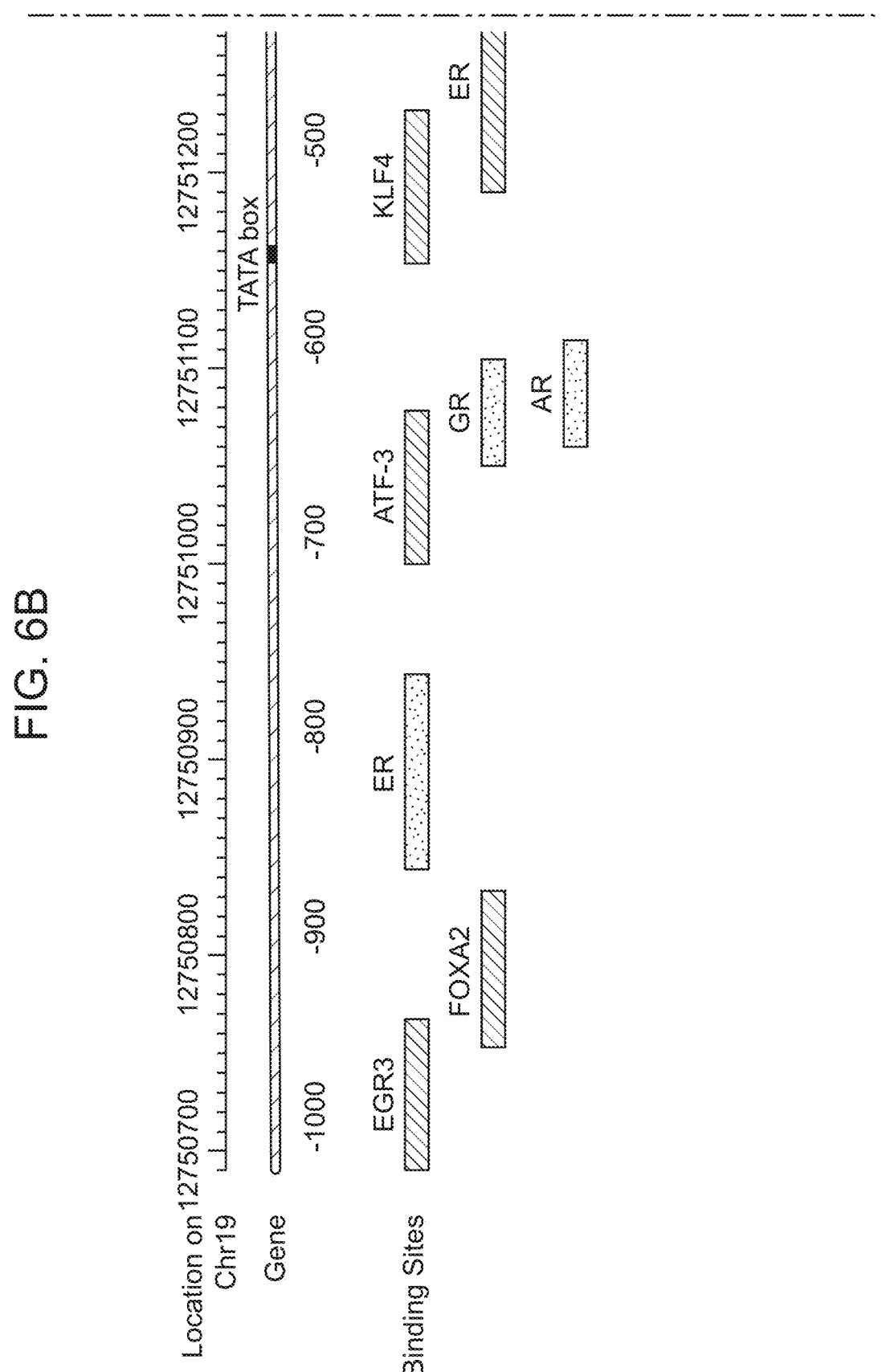
Figure 6C:
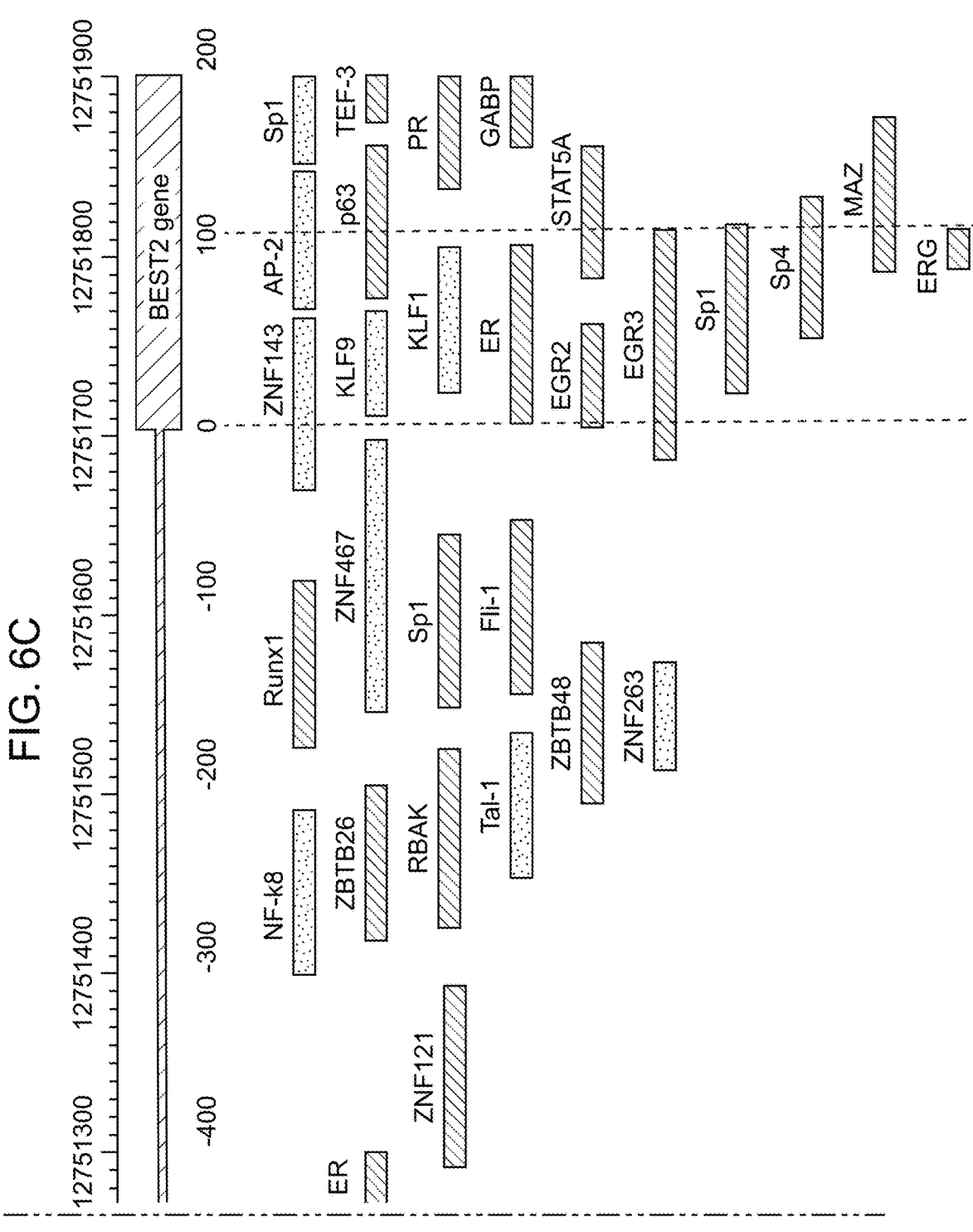

Transcription factor binding was investigated for the sequence regions of each of the tested 14 promoters starting approximately 1.1 kb upstream of the BEST2 gene with some overlap into the BEST2 gene (FIG. 6A). The locations of transcription factors known to bind within the 1.2 kb region tested to drive GFP expression specifically in the NPCECs and in the BEST2 gene are shown in FIG. 6B.

Example 5

Figure 7C:
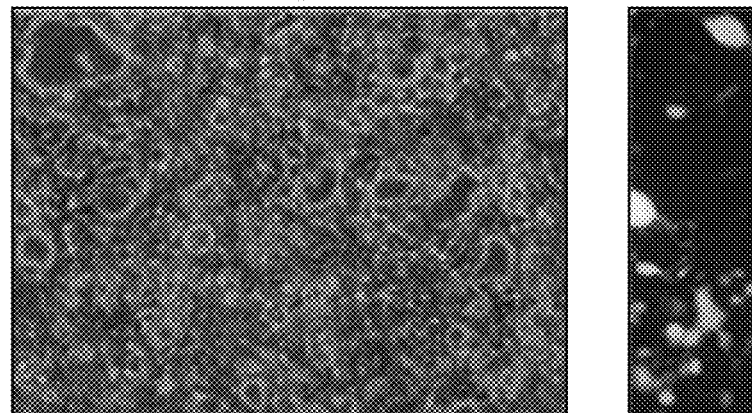
Figure 7C:
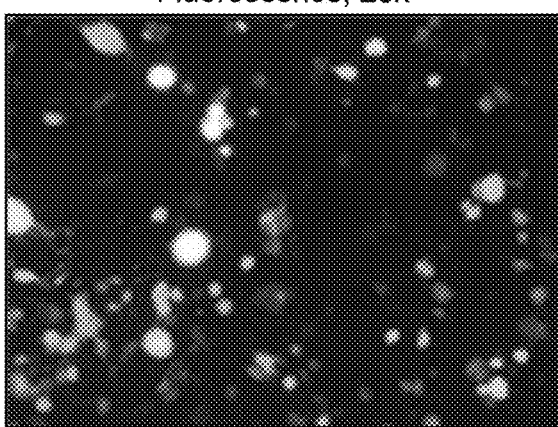
Figure 7C:
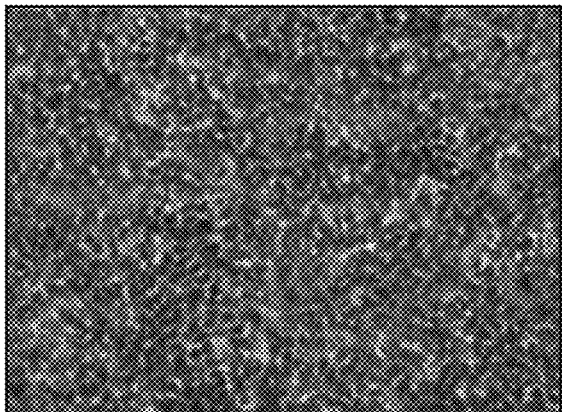
Figure 7C:
Figures 7D, 7E:
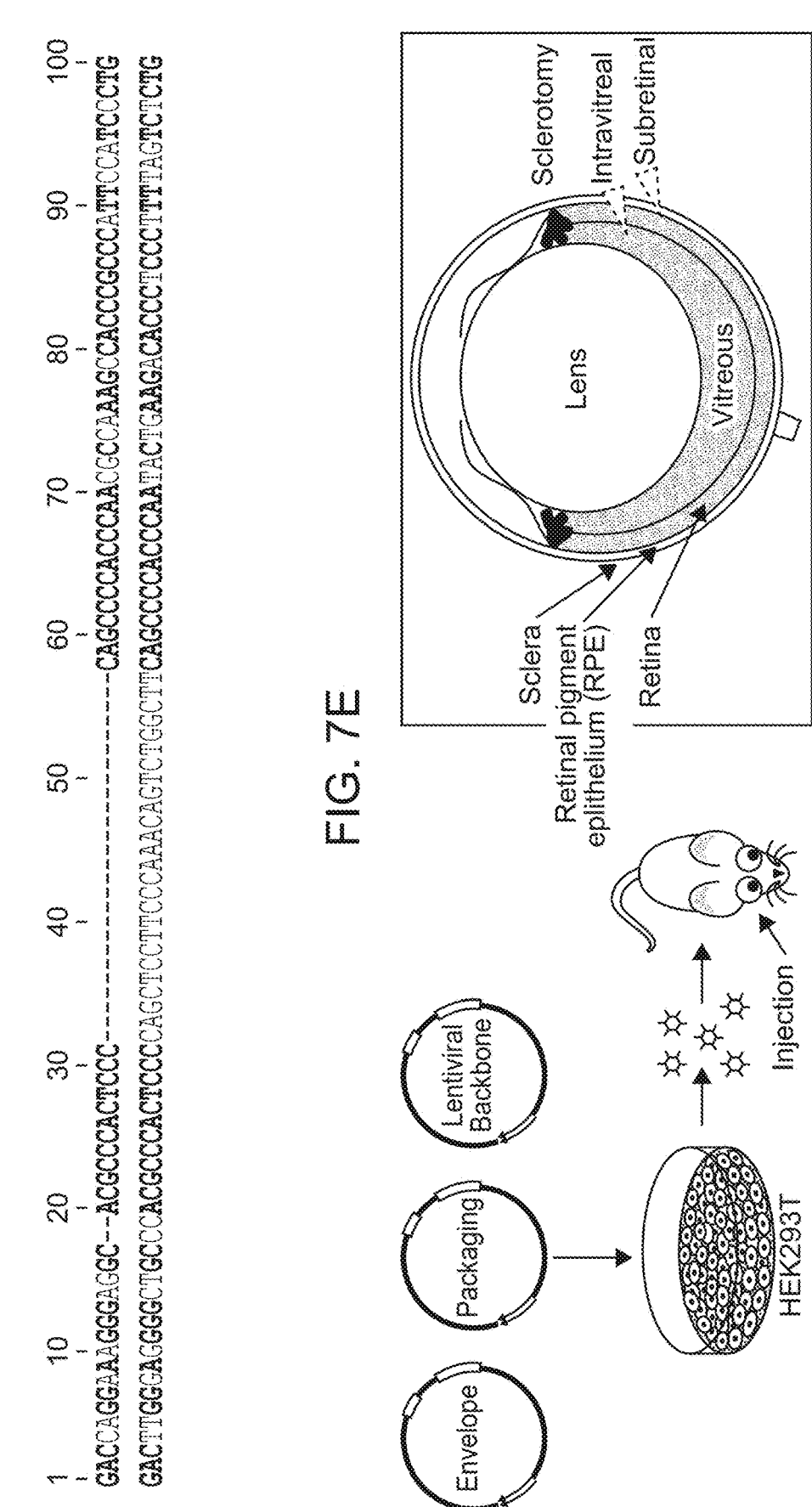

In Vivo Preferential Targeting of the Non-Pigmented Ciliary Epithelial Cells Using Intravitreal Injections of a VMD2L1-Drived Green Fluorescent Protein Lentivirus was created containing green fluorescent protein (GFP) driven by either the constitutively active EF1a (elongation factor 1 alpha) promoter or promoter 13 for the BEST2 gene. Lentiviruses effectively transduced HEK293T cells and had a titer of $4 \times 10^8$ for EF1a and $1.2 \times 10^8$ for promoter 13 viral vectors. Lentiviruses created in HEK293T cells will undergo intravitreal injection into a mouse eye, to show specificity of GFP expression in the non-pigmented ciliary epithelial cells (FIG. 7D).

Example 6

Figure 8D:
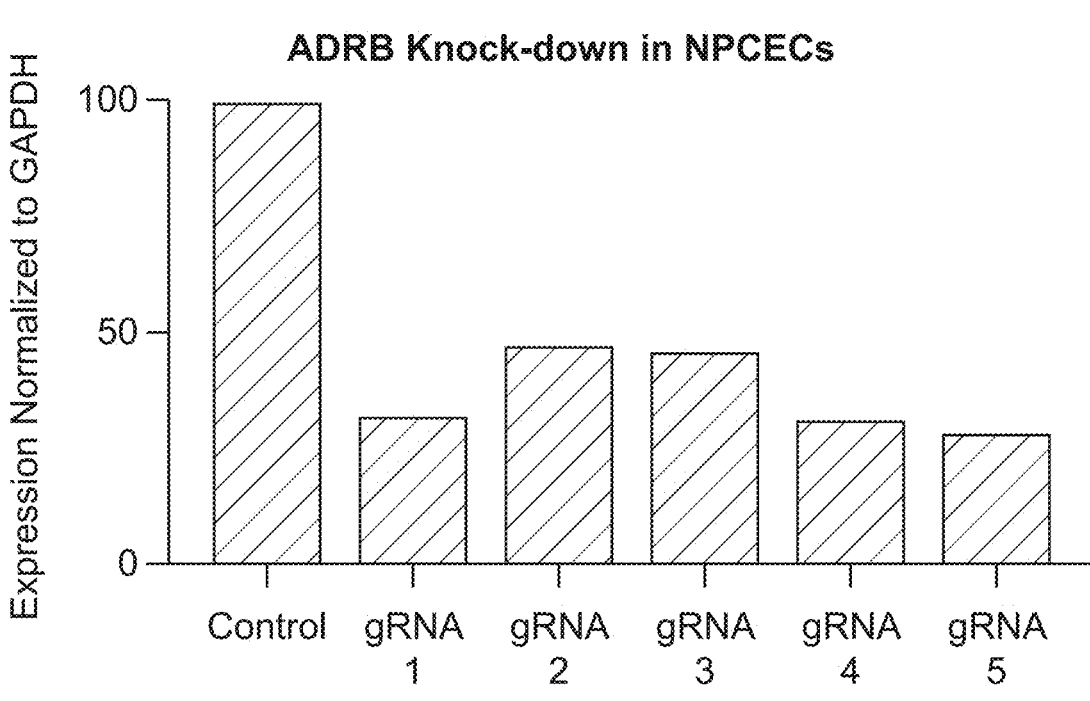
Figure 8E:
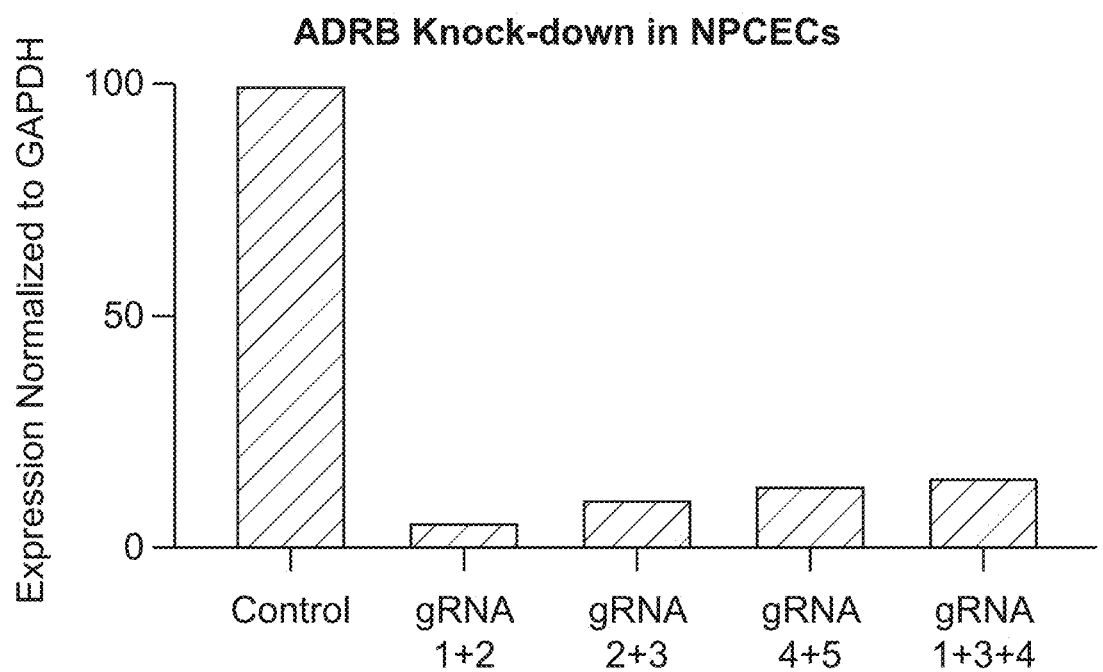

CRISPR/Cas9-Mediated Knockdown of Beta-Adrenergic Receptor 2 in the Non-Pigmented Ciliary Epithelial Cells Human NPCECs were transfected with a lentiviral construct containing a guide RNA (gRNA) against the beta-adrenergic receptor 2 (ADRB2) and SpCas9 driven by the constitutively active EFS (elongation factor 1 alpha short) promoter (FIG. 8A). NPCECs transfected with control (no gRNA) or gRNAs 1-5 for ADRB2 were treated for at least 3 days with puromycin and then collected for western blot analysis. ADRB2 protein bands were normalized to GAPDH and each gRNA knocked down ADRB2 protein by approximately 50% (FIG. 8B). NPCECs transfected with control (no gRNA) or double and triple gRNAs 1-5 for ADRB2 were treated for at least 3 days with puromycin and then collected for western blot analysis. ADRB2 protein bands were normalized to GAPDH and using two gRNAs knocked down ADRB2 protein by approximately 80-90%, with gRNA 1 and gRNA 2 showing the strongest knockdown of ADRB2 protein (FIGS. 8C-8E).

What is claimed is:

1. A recombinant promoter construct comprising a minimal BEST2 promoter and a transcriptional start site (TSS), wherein the recombinant promoter construct is transcriptionally active in non-pigmented ciliary epithelial cells (NPCECs) and not in retinal pigment epithelial cells, wherein the recombinant promoter construct has a non-native configuration with a non-native spacing between the minimal BEST2 promoter and the TSS, and wherein the minimal BEST2 promoter consists of:
  a) the nucleotide sequence corresponding to positions 12,751,703-12,751,803 of human chromosome 19,
  b) the nucleotide sequence of SEO ID NO: 1, or
  c) a nucleotide sequence having at least 95% sequence identity to the nucleotide sequence of SEO ID NO: 1, wherein the promoter is capable of NPCEC-specific transcription.

2. The construct of claim 1, further comprising one or more transcription factor binding sites in addition to transcription factor binding sites in the minimal BEST2 promoter.

3. The construct of claim 2, wherein the one or more transcription factor binding sites are selected from the group consisting of ZNF143, AP-2, KLF9, p63, KLF1, ER, EGR2, STAT5A, EGR3, Sp1, Sp4, MAZ, and ERG.

4. The construct of claim 1, further comprising one or more regulatory sequences operably linked to the minimal BEST2 promoter.

5. The construct of claim 4, wherein at least one regulatory sequence is an enhancer.

6. The construct of claim 4, wherein at least one regulatory sequence makes the recombinant promoter construct inducible.

7. An isolated non-pigmented ciliary epithelial cell (NPCEC) genetically modified with the construct of claim 1.

8. An expression cassette comprising the recombinant promoter construct of claim 1, wherein the expression cassette is capable of providing gene expression in the NPCECs and not in retinal pigment epithelial cells.

9. The expression cassette of claim 8, further comprising an expressible sequence operably linked to the minimal BEST2 promoter.

10. The expression cassette of claim 9, wherein the expressible sequence encodes a polypeptide or a regulatory RNA.

11. The expression cassette of claim 10, wherein the polypeptide is a sequence specific endonuclease.

12. The expression cassette of claim 11, wherein the sequence specific endonuclease is a genome-editing enzyme.

13. The expression cassette of claim 12, wherein the genome-editing enzyme is a CRISPR associated protein 9 (Cas9) polypeptide, a zinc finger nuclease, a TAL effector nuclease, or an enzymatically inactive type II CRISPR/Cas polypeptide.

14. The expression cassette of claim 9, wherein the expressible sequence encodes a Cas9 guide RNA.

15. The expression cassette of claim 9, further comprising a viral T2A peptide or IRES sequence operably linked to the minimal BEST2 promoter.

16. The expression cassette of claim 15, wherein the construct is multicistronic comprising a first expressible sequence encoding a Cas9 polypeptide and a second expressible sequence encoding a Cas9 guide RNA operably linked to the minimal BEST2 promoter.

17. The expression cassette of claim 8, wherein the construct further comprises a nucleotide sequence encoding a reporter, wherein the nucleotide sequence encoding the reporter is operably linked to the minimal BEST2 promoter.

18. An expression vector comprising the expression cassette of claim 8.

19. The expression vector of claim 18, wherein the expression vector is a viral vector.

20. The expression vector of claim 19, wherein the viral vector is a lentiviral vector.

21. The expression vector of claim 20, wherein the vector comprises a long-terminal repeat (LTR), a Ψ packaging signal, a rev response element (RRE), and a central polypurine tract (cPPT).

22. The expression vector of claim 18, further comprising a selection marker, a Woodchuck hepatitis virus post-transcriptional regulatory element (WPRE), a mammalian origin of replication, a multiple cloning site, a polyadenylation site, or an SV40 early promoter, or any combination thereof.

23. The expression vector of claim 18, wherein the expression vector is a DNA or RNA expression vector.

24. The expression vector of claim 18, wherein the construct comprises a polypeptide-encoding sequence or a Cas9 guide RNA-encoding sequence operably linked to the minimal BEST2 promoter.

25. A method of localizing expression of an expressible sequence to NPCECs in a mammalian subject, the method comprising introducing the expression vector of claim 18 into an eye of the subject, wherein the expressible sequence is selectively expressed in the NPCECs.

* * * * *

SEQUENCE LISTING

<160> NUMBER OF SEQ ID NOS: 2

<210> SEQ ID NO 1
<211> LENGTH: 100
<212> TYPE: DNA
<213> ORGANISM: Homo sapiens -continued

```
<400> SEQUENCE: 1
tgaagctaca gcctagccga gggaggagga ccaggaaagg gaggcacgcc cactccccag       60
ccccacccaa cgccaaagcc acccgcccat tccatccctg                           100

<210> SEQ ID NO 2
<211> LENGTH: 100
<212> TYPE: DNA
<213> ORGANISM: Mus musculus

<400> SEQUENCE: 2
gacttgggag gggctgccca cgcccactcc ccagctcctt cccaaacagt ctggcttcag       60
ccccacccaa tactgaagac accctccctt ttagtctctg                           100
```